United States Patent
Gottschling et al.

(10) Patent No.: US 12,156,874 B2
(45) Date of Patent: Dec. 3, 2024

(54) INHIBITORS OF TRPC6

(71) Applicant: Boehringer Ingelheim International GmbH, Ingelheim am Rhein (DE)

(72) Inventors: Dirk Gottschling, Mittelbiberach (DE); Thierry Bouyssou, Warthausen (DE); Niklas Heine, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 670 days.

(21) Appl. No.: 17/602,803

(22) PCT Filed: Apr. 7, 2020

(86) PCT No.: PCT/EP2020/059854
§ 371 (c)(1),
(2) Date: Oct. 11, 2021

(87) PCT Pub. No.: WO2020/208002
PCT Pub. Date: Oct. 15, 2020

(65) Prior Publication Data
US 2022/0152023 A1 May 19, 2022

(30) Foreign Application Priority Data
Apr. 12, 2019 (EP) ..................... 19168845

(51) Int. Cl.
*A61K 31/501* (2006.01)
*C07D 401/14* (2006.01)

(52) U.S. Cl.
CPC .......... *A61K 31/501* (2013.01); *C07D 401/14* (2013.01)

(58) Field of Classification Search
CPC ............................ A61K 31/501; C07D 401/14
USPC ..................................... 514/252.03
See application file for complete search history.

(56) References Cited

U.S. PATENT DOCUMENTS

2019/0169167 A1* 6/2019 Bouyssou ............... A61K 31/45

FOREIGN PATENT DOCUMENTS

WO 2019169168 A1 9/2019
WO 2020208002 A1 10/2020

OTHER PUBLICATIONS

Sawamura, Screening of transient receptor potential canonical, Molecular Pharmacology, vol. 89, 2016.
Desai, TRP channels and mice deficient in TRP channels, Eur. J. Physiol. vol. 451, 2005.
Clapham, The TPR ion Channel Family, Nat. Rev. Neuro Sci, 2001, p. 387-396.
Clapham, TPR channels as cellular sensors, Nature, 2003.
Hofmann, Direct activation of human TRPC6 and TRP3 channels, 1999, vol. 3, p. 259-263.
Winn, A mutation in the TRPC6 cation channel, Science, 2005, p. 1801-1804.
Reiser, TRPC6 is a glomular slit diaphragm association channel requied, Nature Genet, 2009. p. 739-744.
Moeller, Induction of TRPC6 Channel, Amer. Society of Nephrology, 2007.
Sadowski, A single-Gene Cause in 29.5 of cases of Steroid-Resistant Nephrotic Syndrome, JASN, vol. 36, 2015.
Thilo, VEGF regulates TRPC Channels in podocytes, Nephrol. Dial. Transplant, vol. 27, 2012.
Eckel, TRPC6 enhances Angiostentin Il-induced Albuminuria, JASN, vol. 22, 2011.
Krall, Podocyte Specific overexpressionof wild type, PLOS, vol. 5, 2010.
Yu, Enhanced expression of transient receptor potential channels, PNAS, vol. 101, 2004.
Ku, Expression of transient receptor Channel proteins, Society for Gynecologic Proteins, 2006.
Yu, A functional single-nucleotide Polymorphism in the TRPC6 gene promoter, Circulation, 2009.
Clarson, Store operated Ca2 entry in first trimester and term human placenta, J. Physiol., vol. 2, 2003.
Kunichika, Bosentan Inhibits transient receptor potential, Amer. J. of Respiratory and Critical Care Med., vol. 170, 2004.
Chigrupati, Receptor ChannelTRPC6 is a kep Mediator, Cancer Research, vol. 70, 2010.
International Search Report PCT/EP2020/059854 mailed May 2, 2019.
Wang, Effects of chronic exposure to cigarette smoke on cannonical transient receptor potential expression in rat, Am. J. Physiol, vol. 306, 2013.
Ding, Essential Role of TRPC6 Channels in G2/M Phase Transition, JNCI, vol. 102. 2010.

(Continued)

*Primary Examiner* — Kristin A Vajda
(74) *Attorney, Agent, or Firm* — David L. Kershner

(57) ABSTRACT

The present invention relates to compounds of formula (I) wherein A, X, $R^1$, $R^2$, $R^3$, $R^4$ and $R^5$ are as defined herein, and pharmaceutically acceptable salts thereof. The invention also relates to pharmaceutical compositions comprising these compounds, methods of using these compounds in the treatment of various diseases and disorders, such as hypertension, preeclampsia, restenosis, a cardiac or respiratory condition, renal disease, liver disease, muscular dystrophy, fibrotic disorders, pain, ischemia or ischemic reperfusion injury, and cancer.

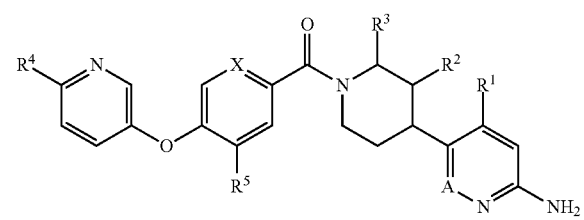

(I)

13 Claims, No Drawings

(56) References Cited

OTHER PUBLICATIONS

Finney, Expression of Transient receptor potention c6 channels in human lung micrphages, Am. J. Respir. Cell Mol. Biol. vol. 43, 2008.
Wan, Expression of transient receptor potential channel 6 in cervical cancer, ONCO targets and therapy, vol. 5, 2012.
Antigny, Transient receptor ptoential canonical channel 6 links ca2 mishandling to cystic fibrosis, Am. J. Respir. Cell mol. Biol. vol. 44, 2011.
Dhennin, High Expression of transient receptor potential channel, Cellular Physiology and Biochem, vol. 28, 2011.
Lei, The role of mechanical tension on lipid raft dependent PDGF-induced TRPC6 activation, Biomaterials, vol. 35, 2014.
Song, Critical Role of TRPC6 channels in the delvelopment of human renal cell carcinoma, Mol. Biol. Rep. vol. 40, 2013.
Weissmann, Activation of TRPC6 channels is essential for lung ischaemia-reperfusion induced oedema in mice, 2014.
De Quiros, ID of TRPC6 as a possible candidate target gene, BMC cancer, vol. 13, 2013.
Tauseef, TLR4 acivation of TRPC6-dependent calcium signaling mediated endotoxin-infuced lung vascular permeability and inflammation, Jem, vol. 209, 2012.
Zhang, High expression of transient potential receptor C6 correlated with poor prognosis in patients wirh esophageal squamous cell cancer, Med. Oncol., 2013.
Kuwahara, TRPC6 fills a calcineurin signalling curcuit, JCI, 2006.
Wen, Regulation of multi drug resistance in hepatocellular carcinoma cells is TRPC6/Calcium dependent, Scientific Reports, 2015.
Xie, Cardioprotection by Klotho through downregulation of TRPC6 channels in the mouse heart, Nature Communcations, 2012.
Iyer, Receptor channel TRPC6 orchestrate the activation of human hepatic stellate cell under hypoxia condition, Experimental Cell Research, vol. 336, 2015.
Xie, Soluble Klotho Protects against uremic Cardiomyopathy, JASN, 2015.
Seo, Hyperactive Adverse Mechanical StressRespinses in Dystophic heart are coupled to transient receptor potential canonical 6, Integrative Physiology, 2021.
Wu, TRPC channels are necessary mediators of pathologic cardiac hypertrophy, PNAS, vol. 107, 2010.
Davis, A TRPC6 dependentpathway for myofibeoblast transdifferentiation and wound healing in vivo, Cell press, vol. 23, 2012.
Seo, Combined TRPC6 and TRPC6 blockade by selective small molecule or genetic deletion, PNAS, vol. 111, 2014.
Haber, TRPC1 and TRPC6 channels cooperate with TRPV4 to mediate mechanical Hyperalgesia, Neurobiology of Disease, 2009.
Rosenbaum. Hypercholesterolemia inhibits Reendothelialization of arterial injuries by TRPC channels, J. Vasc. Surg., vol. 62, 2015.
Chaudhuri, Elucidation of a TRPC6-TRCP5 Channel Cascade that restricts Endothelial cell movement, Mole. Biol. of the Cell, vol. 19, 2008.
Bergdahl, Plasticity of TRPC expression in arterial smooth muscle, Am. J. Cell Physiol, vol. 288, 2004.
Zhang, Micro-MRNA-26a prevents endothelial cell apoptosis by directly targeting TRPC6, Scientific Reports, 2015.
Johannson, Cerebrovascular endothelin-I hyperactivity is associated with transient receptor potential canonical channels 1 and 6, Acta Physiol. vol. 214, 2015.
Schlondorff, TRPC6 mutations associated with focal segmental glomerulosclerosis cause constitutive activation of NFAT-dependent transcription, Am J. Physiol Cell Physiol, vol. 296, 2009.

\* cited by examiner

INHIBITORS OF TRPC6

FIELD OF THE INVENTION

The present invention relates to pharmaceutical compounds, compositions, and methods for the treatment of cardiac and respiratory conditions, renal disease, liver disease, muscular dystrophy, fibrotic disorders, pain, ischemia or ischemic reperfusion injury, and cancer, as well as inhibiting the Transient Receptor Potential C6 ion channel (TRPC6).

BACKGROUND

A variety of ion channel proteins exist to mediate ion flux across cellular membranes. The proper expression and function of ion channel proteins is essential for the maintenance of cellular function, intracellular communication, and the like. An important aspect of achieving cellular homeostasis is the maintenance of appropriate ion concentrations in various cell types during development and in response to numerous stimuli. Large numbers of diverse types of ion channels act to maintain cellular homeostasis by moving ions into and out of cells across the plasma membrane, and within cells by moving ions across membranes of intracellular organelles including, for example, the endoplasmic reticulum, sarcoplasmic reticulum, mitochondria and endocytic organelles including endosomes and lysosomes. Numerous diseases are the result of dysregulation of membrane potential or aberrant calcium handling. Given the central importance of ion channels in modulating membrane potential and ion flux in cells, identification of agents that can promote or inhibit particular ion channels is of great interest as research tools and as possible therapeutic agents.

One such channel is the Transient Receptor Potential C6 (TRPC6) channel. TRPC6 belongs to the larger family of TRP ion channels (see, Desai et al., 2005 Eur J Physiol 451:11-18; Clapham et al., 2001 Nat Rev. Neurosci 2:387-396; Clapham, 2003 Nature 426: 517-524). TRPC6 is a calcium permeable channel, specifically a non-selective calcium permeable cation channel. In addition to calcium ions, TRPC6 channels are permeable to other cations, for example sodium. Thus, TRPC6 channels modulate not only intracellular calcium concentration, but also membrane potential by modulating the flux of cations including calcium and sodium ions. Although non-selective cation channels such as TRPC6 modulate, among other things, calcium ion flux, they are mechanistically distinct from voltage-gated calcium channels. Generally, voltage-gated calcium channels respond to depolarization of the potential difference across the membrane and can open to permit an influx of calcium from the extracellular medium and a rapid increase in intracellular calcium levels or concentrations. In contrast, non-selective cation channels such as TRPC6 are generally signal transduction gated, long-lasting, and produce less rapid changes in ion concentration. They show increased activity in response to the production of the second messenger, diacylglycerol (Hofmann et al., 1999). In addition, TRPC6 can respond to changes in pressure. These mechanistic differences are accompanied by structural differences among voltage-gated and cation permeable channels. Thus, although many diverse channels act to regulate ion flux and membrane potential in various cell types and in response to numerous stimuli, it is important to recognize the significant structural, functional, and mechanistic differences among different classes of ion channels.

TRPC6 function has been implicated in, among other things, the modulation of myogenic tone. TRPC6 is highly expressed in smooth muscle cells, vascular smooth muscle cells, endothelial cells, cardiomyocytes, pulmonary arteries, the aorta, heart, liver, brain, and kidney. The expression of TRPC6, along with experiments conducted in knock-out mice and cells in culture, suggest that TRPC6 may provide a useful target for the treatment of hypertension and other cardiac and vascular conditions, preeclampsia.

Mutation in the human TRPC6 channel can cause focal segmental glomerulsclerosis (FSGS) (Winn et al., 2005, Reiser et al., 2005). These mutations that are reported to be gain-of-function (Reiser et al., 2005), are sufficient to induce disease. In addition, elevated TRPC6 expression has been associated with nephrotic syndrome, minimal change disease, and diabetic nephropathy (Moller et al., 2007, Thilo et al., 2011), or other kidney conditions.

Based on its expression and work implicating it in TGF-B signaling, TRPC6 is also thought to be important in respiratory conditions, restenosis, liver disease, muscular dystrophy, fibrotic disorders, pain, ischemia and ischemic reperfusion injury, and certain forms of cancer.

Yu et al. studied TRPC6 channels for a role in mediating the pulmonary artery smooth muscle cell proliferation that can lead to idiopathic pulmonary arterial hypertension (IPAH). Pulmonary vascular medial hypertrophy caused by excessive pulmonary artery smooth muscle cell (PASMC) proliferation is a major cause for the elevated pulmonary vascular resistance in patients with IPAH. The authors found that TRPC6 was highly expressed and TRPC3 was minimally expressed in PASMC from healthy lung tissue. However, in lung tissue from IPAH patients, mRNA and protein expression of TRPC3 and TRPC6 were significantly elevated in comparison to that in normotensive patients. Furthermore, proliferation of PASMC cells derived from IPAH patients was markedly reduced following incubation with TRPC6 siRNA. Based on these results, the authors concluded that TRPC6 may be important in mediating proper PASMC proliferation, and that dysregulation of TRPC6 may lead to increased PASMC proliferation and pulmonary vascular medial hypertrophy observed in IPAH patients (Yu et al., 2004 Proc Natl Acad Sci 101(38):13861-6). Further support is provided by the observation that in IPAH patients the frequency of a single-nucleotide polymorphism in the promoter of TRPC6 which increases expression was significantly higher when compared to normal subjects (Yu, et al., 2009 Circulation 119: 2313-22).

Additional evidence implicating TRPC6 dysregulation in IPAH comes from studies of bosentan, a dual endothelin receptor blocker that has been used clinically to treat IPAH. This inhibitor decreases proliferation of PASMCs, but the mechanism by which this occurs is unclear. Interestingly, bosentan both decreases proliferation of PASMC and also decreases expression of TRPC6 in lung tissue of IPAH patients (Kunichika et al., 2004 Am J Respir Crit Care Med 170(10):1101-7).

Chronic exposure of cigarette smoke (CS) to rats resulted in an increase in TRPC6 mRNA and protein expression in distal pulmonary arteries and similar effects were observed using PASMCs in vitro. Nicotine treatment of cultured rat PASMCs upregulated TRPC6 expression and increased intracellular calcium levels, both of which were reduced by TRPC6 siRNA silencing (Wang et al., 2014 Am J Physiol Cell Physiol 306:C364-73). These results suggest a role for TRPC6 in CS-induced lung injury.

Evidence supports a role of TRPC6 in additional pulmonary disorders. In alveolar macrophages from patients with chronic obstructive pulmonary disease (COPD), TRPC6 expression was found to be elevated when compared with controls (Finney-Hayward et al., 2010 Am J Respir Cell Mol Biol 43:296-304). In human cystic fibrosis epithelial cells, the TRPC6-mediated calcium influx is abnormally increased and may contribute to the hypersecretion of mucus. siRNA-TRPC6 was able to reduce this abnormal calcium influx (Antigny et al. 2011 Am J Resp Cell Mol Biol, 44:83-90). In mouse lung fibroblasts, the pro-fibrotic activity of PDGF is dependent on the activation of TRPC6, suggesting that TRPC6 inhibition would reduce lung fibrosis (Lei et al., 2014 Biomaterials 35:2868-77). A role of TRPC6 in pulmonary endothelial cell function was demonstrated in mouse lung models of ischemia-reperfusion induced-edema and lipopolysaccharide-induced inflammation in whichTRPC6 deficiency was able to reduce acute lung injury by preserving endothelial barrier function (Weissmann et al., 2011 Nat Comm, 3:649-58 and Tauseef et al., 2012 J Exp Med 209:1953-68).

Recent studies also implicate the role of TRPC6 in other cardiac conditions, including cardiac hypertrophy. The hearts of patients with dilated cardiomyopathy have elevated TRPC6 mRNA expression when compared with normal hearts (Kuwahara et al., 2006 J Clin Invest 116:3114-26). In mouse models of cardiac hypertrophy, TRPC6 cardiac mRNA levels are elevated by pressure overload (Kuwahara et al., 2006 J Clin Invest 116:3114-26), chronic isoproterenol treatment (Xie et al., 2012 Nat Commun 3:1238), and uremic cardiomyopathy induced by partial nephrectomy (Xie et al., 2015 J Am Soc Nephrol 26:1150-60). Furthermore, cardiac-specific overexpression of TRPC6 in the cardiomyoctes of transgenic mice induced cardiac hypertrophy and premature death (Kuwahara et al., 2006 J Clin Invest 116:3114-26).

Wu and colleagues found that transgenic mice expressing dominant-negative TRPC6 in a cardiac-specific fashion had an attenuated cardiac hypertrophic response following either neuroendocrine agonist infusion or pressure-overload simulation, indicating that TRPC6 is a component of channel complexes that are essential mediators of hypertrophy (VVu et al., 2010 Proc Natl Acad Sci. 107:7000-05). Small molecule drugs targeting TRPC6 have also recently begun to show promise in treating cardiac conditions. For example, Seo and coworkers demonstrated that TRPC6 and TRPC3 antagonists (GSK2332255B and GSK833503A) exhibited dose-dependent inhibition of cell hypertrophy signaling in neonatal and adult cardiac myocytes (Seo et al., 2014 Proc Natl Acad Sci 111:1551-1556). Similarly, mice deficient for TRPC6 were protected from isoproterenol-induced cardiac hypertrophy (Xie et al., 2012 Nat Commun 3:1238).

Reducing TRPC6 activity may be beneficial for the treatment of cardiovascular disease. In vitro, atheroprone shear stress-induces increased TRPC6 mRNA levels in human vascular endothelial cells (EC) when compared to atheroprotective flow conditions (Thilo, et al., 2012 Hypertension 59:1232-40). EC migration is important for healing after arterial injury, and lysophosphatidylcholine-mediated inhibition of EC migration was prevented in vitro in cells from TRPC6 deficient mice. Furthermore, high cholesterol diet combined with carotid injury did not impair healing in TRPC6 deficient mice when compared with wild-type controls (Rosembaum et al., 2015 J Vasc Surg 62:1040-47 and Chaudhuri et al., 2008 Mol Biol Cell 19: 3203-11). Similarly, balloon dilatation-induced injury of human internal mammary arteries ex vivo resulted in increased TRPC6 mRNA levels when compared with undilated arteries (Bergdahl et al., 2005 Am J Physiol Cell Physiol 288:C872-80).

Apoptosis of endothelial cells is involved in the initiation and progression of atherosclerotic lesions, and oxidized low-density lipoprotein-induced apoptosis of human aortic ECs was demonstrated to be dependent on TRPC6 (Zhang et al., 2015 Sci Rep 5:9401-10). In a rat model of forebrain ischaemia, TRPC6 mRNA levels were increased in vascular SMCs and correlated with reduced cerebral blood flow (Johannson et al., 2015 Acta Physiol 214:376-89).

Studies by Reiser, Winn, and Schlöndorff identified mutations in TRPC6 in patients as being causative in FSGS (Reiser et al., 2005 Nature Genet 37:739-744; Winn et al., 2005 Science 308:1801-1804; Schlöndorff et al., 2009 Am J Physiol Cell Physiol 296:C558-69). Subsequent studies identified additional TRPC6 mutations associated with steroid-resistant nephrotic syndrome (C. Sadowski et al., 2014 J Am Soc Nephrol 26:1279-89). Further studies demonstrated that TRPC6 is important in normal podocyte function by controlling calcium influx and nuclear factor of activated T cell activation in which elevated current through the channel is associated with renal injury and the induction of proteinuria (Moller et al., 2007 J Am Soc Nephrol 18:29-36 and Schlöndorff et al., 2009 Am J Physiol Cell Physiol 296:C558-69). In addition to Gain of Function mutations, it has been shown that expression of TRPC6 is elevated in human chronic kidney diseases including FSGS, minimal change disease, membraneous glomerulonephritis, and diabetic nephropathy (Moller et al., 2007 J Am Soc Nephrol 18:29-36 and Thilo et al., 2011 Nephrol. Dial. Transplant 27:921-9) as well as in mouse models of podocyte injury (Moller et al., 2007 J Am Soc Nephrol 18:29-36). TRPC6 deficient mice have been demonstrated to have reduced angiotensin II (Ang II)-induced albuminuria (Eckel et al., 2011 J Am Soc Nephrol 22:526-35) whereas transgenic podocyte-specific expression of human GoF mutations in mice induces albuminuria and glomerular lesions (Krall et al., 2010 PLoS ONE e12859 and Canales et al., 2015 Brit J Medicine Med Res 5:1198-1212). Consequently, inhibition of TRPC6 may be useful in the treatment of chronic kidney diseases. These findings not only suggest that TRPC6 normally functions to maintain proper kidney function, but also implicates TRPC6 as a specific cause of at least certain cases of FSGS. Based on the likely role of TRPC6 in kidney function, TRPC6 inhibitor compounds can be used in treating or ameliorating chronic kidney diseases or conditions caused (in whole or in part) by TRPC6 dysfunction. Additionally, TRPC6 inhibitor compounds can be used in treating or ameliorating symptoms of kidney diseases (e.g., hypertension, proteinuria, etc.), regardless of the cause of the disease.

TRPC6 is expressed in the myometrium and placenta during pregnancy (Ku et al., 2006 J Soc Gynecol Investig 13:217-225; Clarson et al., 2003 J Physiol 550:515-528). As such TRPC6 may contribute to maintaining proper myogenic tone in the placenta and/or in maintaining proper fetal and maternal blood pressure during pregnancy.

Recent evidence has emerged implicating TRPC6 in certain forms of cancer. Several groups have established that TRPC6 expression is elevated in cells taken from patients with gliobastoma multiforme, the most frequent and incurable type of brain cancer (Chigurupati, et al., 2010 Cancer Res, 70:418-427; Ding et al., 2010 J Natl Cancer Inst. 102:1052-1068).

Similarly, Ding et al. found elevated levels of TRPC6 in human glioma cells, and inhibition of TRPC6 pharmacologically or with a dominant-negative mutant suppressed cell growth in vitro. In two xenograft models of human gliomas, lentiviral-mediated expression of dominant-negative TRPC6 in the tumor cells prior subcutaneous or intracranial implantation reduced tumor volume when compared to controls (Ding et al., J. Natl. Cancer Inst. 2010, 102, 1052-1068). Increased levels of TRPC6 was also found to be associated with cervical cancer (VVan et al, 2012 Onco Targets Ther 5:171-176), breast cancer (Dhennin-Duthille et al., 2011 Cell Physiol Biochem 28:813-822), renal cell carcinoma (Song et al, 2013 Mol Biol Rep 40:5115-5122), head and neck squamous cell carcinoma (de Quiros, et al. 2013 BMC Cancer 13:116-127), and esophageal squamous cell carcinoma (Zhang et al., 2013 Med Oncol 30:607), among others. In hepatocellular carcinoma cells, it was demonstrated that doxorubicin, hypoxia, and ionizing radiation increased TRPC6 mRNA expression, and that TRPC6 is found at higher levels in tumor tissues than in the non-involved tissues. Elevated TRPC6 was associated with drug resistance which was diminished by TRPC6 RNA silencing in vitro. Lentiviral delivery of TRPC6 specific short hairpin RNA into Huh7 tumor cells prior to implantation in a mouse subcutaneous xenograft model reduced tumor growth and sensitized the tumors to doxorubicin (Wen et al., 2016 Sci Rep 6:23269). These findings suggest that TRPC6 may be a promising therapeutic target for cancer treatment.

Liver diseases including non-alcoholic steatohepatitis may be treated by reducing TRPC6 activity. Hypoxia increased TRPC6 expression in an human hepatic stellate cell line when compared to normoxic conditions. Using these cells, TRPC6 RNA silencing down-regulated transcripts for alpha smooth muscle actin and collagen 1A1, both of which are associated with fibrosis, in response to hypoxia Oyer et al, 2015 Exp Cell Res 336:66-75).

Inhibition of TRPC6 may provide benefit to patients with Duchenne muscular dystrophy (DMD). In the mdx/utrn$^{+/-}$ model of DMD using isolated cardiomyoctes, TRPC6 deficiency restored the stress-stimulated contractility force and calcium transient response to normal when compared with mice possessing the wild-type TRPC6 gene, suggesting that TRPC6 inhibition will preserve cardiac function in DMD patients (Seo et al., 2014 Circ Res 114:823-32).

Fibrotic disorders may be treated with TRPC6 inhibitors. Overexpression of TRPC6 induced myofibroblast activation while deletion of TRPC6 reduced transforming growth factor beta-induced myofibroblast transformation. Furthermore, TRPC6 deficient mice demonstrated reduced dermal and cardiac wound healing (Davis et al., 2012 Dev Cell 23:705-15).

TRPC6 inhibitors may be useful to reduce the rate of mortality in ARDS, sepsis, severe sepsis and septic shock since the survival rate in the mouse model of systemic sepsis (cecal ligation puncture, CLP) was significantly improved (80% vs 10% in the vehicle group) in TRPC6 deficient mice (Tauseef et al., 2012 J Exp Med 209: 1953-1968)

TRPC6 inhibitors may be useful for the treatment of pain. Spinal delivery of TRPC6 antisense oligonucleotides reduced hyperalgesia induced by mechanical, hypotonic, and thermal stimuli in preclinical pain models (Alessandri-Haber et al., 2009 J Neurosci 29:6217-28).

Modulating a function of TRPC6 provides a means for modulating calcium homeostasis, sodium homeostasis, intracellular calcium levels, membrane polarization (resting membrane potential), and/or cation levels in a cell. Compounds that can modulate one or more TRPC6 functions are useful in many aspects including, but not limited to, maintaining calcium homeostasis; maintaining sodium homeostasis; modulating intracellular calcium levels; modulating membrane polarization (membrane potential); modulating cation levels; and/or treating or preventing diseases, disorders, or conditions associated with calcium homeostasis, sodium homeostasis, calcium or sodium dyshomeostasis, or membrane polarization/hyperpolarization (including hypo and hyperexcitability), and/or treating or preventing diseases, disorders, or conditions associated with regulation or dysregulation of TRPC6 expression or function.

There is a need for highly selective TRPC6 antagonists for treating diseases or disorders that can be alleviated by modulating TRPC6.

BRIEF SUMMARY OF THE INVENTION

The present invention provides novel compounds that modulate TRPC6 and thus are useful for treating a variety of diseases and disorders that can be alleviated by modulating TRPC6 including hypertension, preeclampsia, restenosis, a cardiac or respiratory condition, renal disease, liver disease, muscular dystrophy, fibrotic disorders, pain, ischemia or ischemic reperfusion injury, and cancer. This invention also relates to pharmaceutical compositions comprising these compounds, methods of using these compounds in the treatment of various diseases and disorders, processes for preparing these compounds and intermediates useful in these processes.

In a first embodiment (embodiment one), the inventions relates to compounds of formula (I)

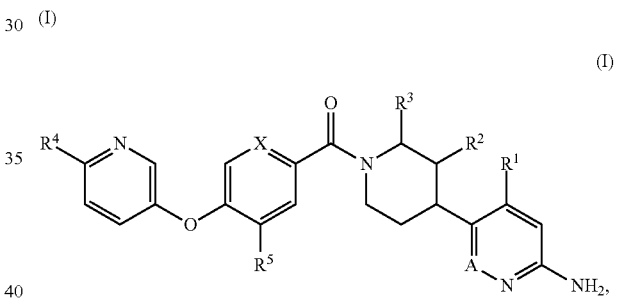

wherein

A is selected from CH or N;

X is selected from CH or N;

$R^1$ is selected from the group consisting of H, —$CH_3$ and —$OCH_3$, $R^2$ is selected from the group consisting of H and —$CH_3$;

$R^3$ is selected from the group consisting of H and —$CH_3$; or $R^2$ and $R^3$ together denote a —$(CH_2)_n$— bridge, wherein n denotes the number 2, 3, 4 or 5, and wherein optionally one —$CH_2$-member is replaced by O, S, —NH— or —N($CH_3$)—, or the —CH($R^3$)—($R^2$)CH— substructure in formula (I) is replaced by a 5-membered heteroaryl group selected from the group consisting of furan, thiophen, pyrrol and N-methyl-pyrrol, which are condensed with the piperine ring of formula (I);

$R^4$ is selected from the group consisting of H, —$CF_3$, and —$OCH_3$;

$R^5$ is selected from the group consisting of H, —F and —$OCH_3$;

and the salts thereof, preferably the pharmaceutically acceptable salts thereof.

In a second embodiment (embodiment two), the inventions relates to compounds of formula (I),
wherein
A is selected from CH or N;
X is selected from CH or N;
$R^1$ is selected from the group consisting of H, —$CH_3$ and —$OCH_3$,
  preferably from the group consisting of H and —$CH_3$;
$R^2$ denotes H and $R^3$ is selected from the group consisting of H and —$CH_3$; or
$R^2$ denotes —$CH_3$ and $R^3$ denotes H;
  preferably $R^2$ denotes H and $R^3$ is selected from the group consisting of H and —$CH_3$;
$R^4$ is selected from the group consisting of H, —$CF_3$, and —$OCH_3$;
  preferably $R^4$ is selected from the group consisting of —$CF_3$, and —$OCH_3$; $R^5$ is selected from the group consisting of H, —F and —$OCH_3$;
  preferably $R^5$ is selected from the group consisting of H and —$OCH_3$;
and the salts thereof, preferably the pharmaceutically acceptable salts thereof.

In a third embodiment (embodiment three), the inventions relates to compounds of formula (I),
wherein
A denotes N
$R^1$ is selected from the group consisting of H and —$CH_3$
$R^4$ is selected from the group consisting of —$CF_3$, and —$OCH_3$;
and X, $R^2$, $R^3$, and $R^5$ are defined as mentioned in embodiment two;
and the salts thereof, preferably the pharmaceutically acceptable salts thereof.

In a forth embodiment (embodiment four), the inventions relates to compounds of formula (I),
wherein
A denotes N;
$R^1$ is selected from the group consisting of H, and —$CH_3$
$R^4$ denotes —$OCH_3$;
and X, $R^2$, $R^3$ and $R^5$ are defined as mentioned in embodiment two;
and the salts thereof, preferably the pharmaceutically acceptable salts thereof.

In a fifth embodiment (embodiment five), the inventions relates to compounds of formula (I),
wherein
A denotes N;
$R^1$ is selected from the group consisting of H, and —$CH_3$
X denotes CH;
$R^4$ denotes —OCH3;
$R^5$ denotes H;
and $R^2$ and $R^3$ are defined as mentioned in embodiment two;
and the salts thereof, preferably the pharmaceutically acceptable salts thereof.

In a six embodiment (embodiment six), the inventions relates to compounds of formula (I),
wherein
A denotes N;
$R^1$ is selected from the group consisting of H, and —$CH_3$
X denotes N;
$R^4$ denotes —$OCH_3$;
$R^5$ denotes H;
and $R^2$ and $R^3$ are defined as mentioned in embodiment two;
and the salts thereof, preferably the pharmaceutically acceptable salts thereof.

The compounds of formula (I) form stereoisomers specified by the following formulas (Ia), (Ib), and (Ic)

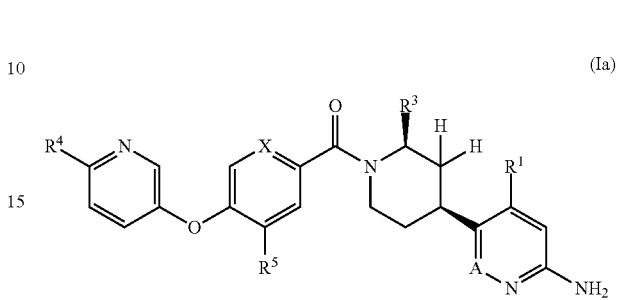

(Ia)

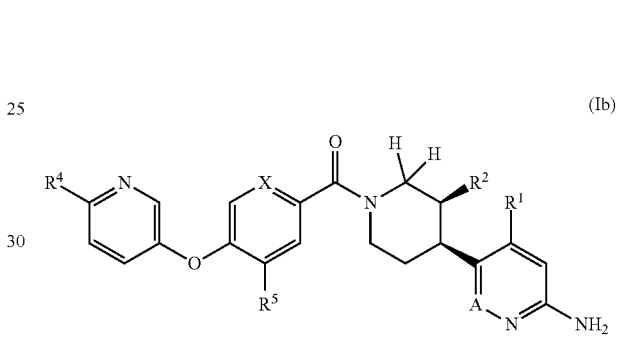

(Ib)

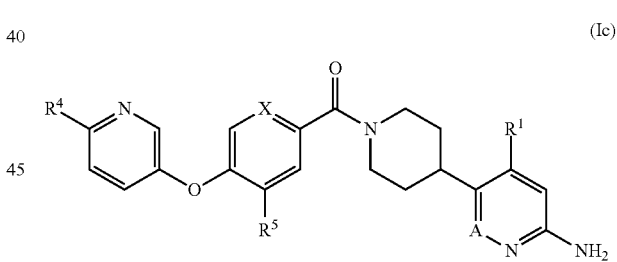

(Ic)

wherein A, X, $R^1$, $R^2$, $R^3$, $R^4$ and $R^5$ are defined as mentioned hereinbefore for embodiments two, three, four, five or six. The invention covers any stereoisomer in substantially pure form as well as any mixture thereof.

DETAILED DESCRIPTION OF THE INVENTION

Table 1 shows the compounds of the invention which can be made by the synthetic schemes and the examples shown in the Synthetic Examples section below.

TABLE 1

| Cpd No. | Structure | Compound Name |
|---|---|---|
| 1 | 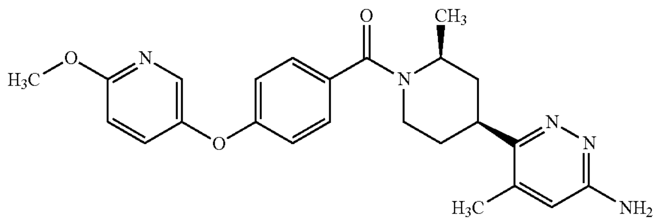 [SMILES: COc1ccc(Oc2ccc(C(=O)N3CC[C@H](c4nnc(N)cc4C)C[C@@H]3C)cc2)cn1] | 6-[(2S,4S)-1-{4-[(6-Methoxypyridin-3-yl)oxy]benzoyl}-2-methylpiperidin-4-yl]-5-methylpyridazin-3-amine |
| 2 | 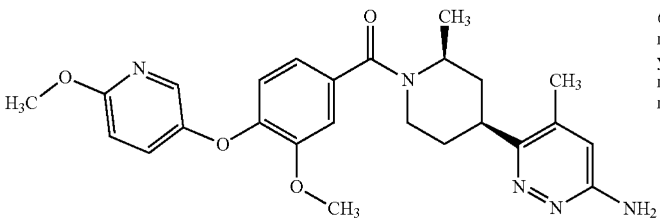 [SMILES: COc1ccc(Oc2ccc(C(=O)N3CC[C@H](c4nnc(N)cc4C)C[C@@H]3C)cc2OC)cn1] | 6-[(2S,4S)-1-{3-Methoxy-4-[(6-methoxypyridin-3-yl)oxy]benzoyl}-2-methylpiperidin-4-yl]-5-methylpyridazin-3-amine |
| 3 | 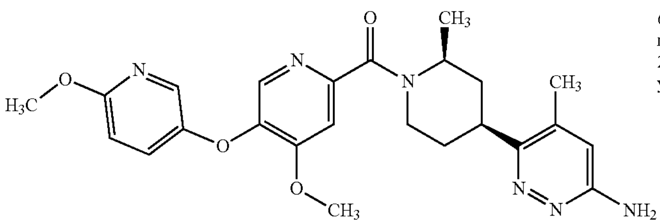 [SMILES: COc1ccc(Oc2cnc(C(=O)N3CC[C@H](c4nnc(N)cc4C)C[C@@H]3C)cc2OC)cn1] | 6-[(2S,4S)-1-{4-Methoxy-5-[(6-methoxypyridin-3-yl)oxy]pyridine-2-carbonyl}-2-methylpiperidin-4-yl]-5-methylpyridazin-3-amine |
| 4 | 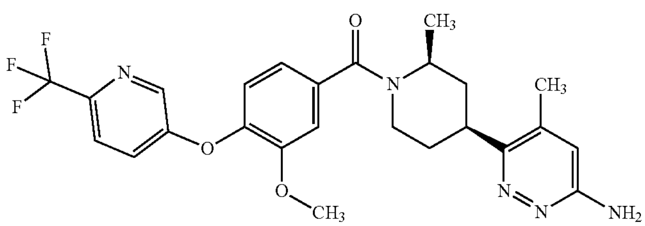 [SMILES: COc1cc(C(=O)N2CC[C@H](c3nnc(N)cc3C)C[C@@H]2C)ccc1Oc1ccc(C(F)(F)F)nc1] | 6-[(2S,4S)-1-(3-Methoxy-4-{[6-(trifluoromethyl)pyridin-3-yl]oxy}benzoyl)-2-methylpiperidin-4-yl]-5-methylpyridazin-3-amine |
| 5 | 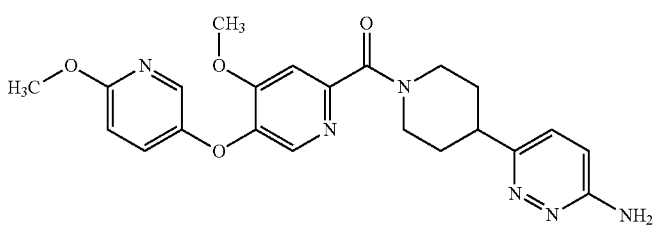 [SMILES: COc1ccc(Oc2cnc(C(=O)N3CCC(c4ccc(N)nn4)CC3)cc2OC)cn1] | 6-(1-{4-Methoxy-5-[(6-methoxypyridin-3-yl)oxy]pyridine-2-carbonyl}piperidin-4-yl)pyridazin-3-amine |
| 6 | 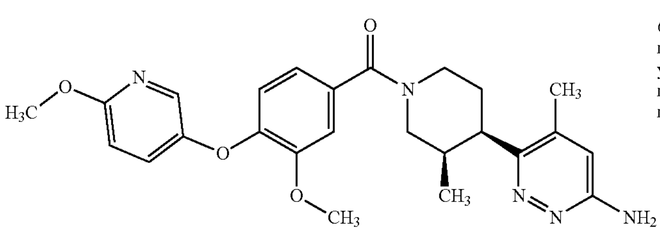 [SMILES: COc1ccc(Oc2ccc(C(=O)N3CC[C@@H](c4nnc(N)cc4C)[C@@H](C)C3)cc2OC)cn1] | 6-[(3R,4R)-1-{3-Methoxy-4-[(6-methoxypyridin-3-yl)oxy]benzoyl}-3-methylpiperidin-4-yl]-5-methylpyridazin-3-amine |
| 7 | 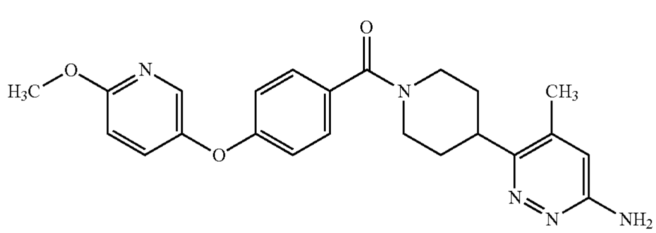 [SMILES: COc1ccc(Oc2ccc(C(=O)N3CCC(c4nnc(N)cc4C)CC3)cc2)cn1] | 6-(1-{4-[(6-Methoxypyridin-3-yl)oxy]benzoyl}piperidin-4-yl)-5-methylpyridazin-3-amine |

TABLE 1-continued

| Cpd No. | Structure | Compound Name |
|---|---|---|
| 8 | 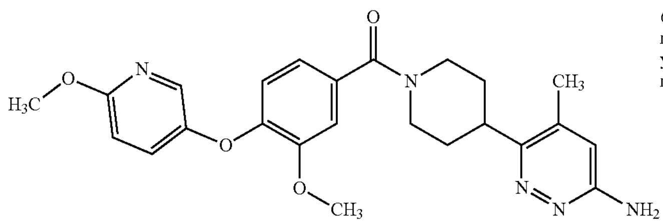 [SMILES: COc1ccc(Oc2ccc(C(=O)N3CCC(c4nnc(N)cc4C)CC3)cc2OC)cn1] | 6-(1-{3-Methoxy-4-[(6-methoxypyridin-3-yl)oxy]benzoyl}piperidin-4-yl)-5-methylpyridazin-3-amine |
| 9 | 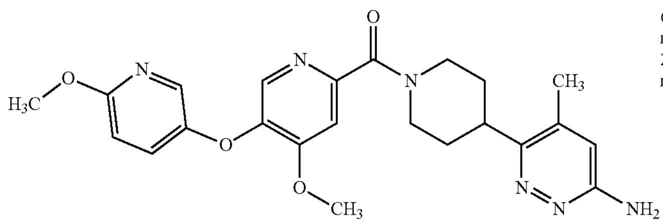 [SMILES: COc1ccc(Oc2cnc(C(=O)N3CCC(c4nnc(N)cc4C)CC3)cc2OC)cn1] | 6-(1-{4-Methoxy-5-[(6-methoxypyridin-3-yl)oxy]pyridine-2-carbonyl}piperidin-4-yl)-5-methylpyridazin-3-amine |
| 10 | 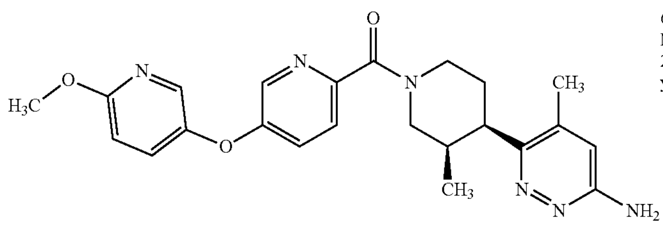 [SMILES: COc1ccc(Oc2ccc(C(=O)N3CC[C@@H](c4nnc(N)cc4C)[C@@H](C)C3)nc2)cn1] | 6-[(3R,4R)-1-{5-[(6-Methoxypyridin-3-yl)oxy]pyridine-2-carbonyl}-3-methylpiperidin-4-yl]-5-methylpyridazin-3-amine |

In one embodiment, the invention relates to any of the compounds depicted in Table 1 above and the pharmaceutically acceptable salts thereof.

The invention further relates to a pharmaceutical composition comprising any one of compounds disclosed in Table 1, and the pharmaceutically acceptable salts thereof, and a pharmaceutically acceptable excipient or carrier.

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In case a compound of the present invention is depicted in form of a chemical name and as a formula in case of any discrepancy the formula shall prevail.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio. As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a The present application provides compounds that can modulate TRPC6 function. Methods employing these compounds are also provided. Certain embodiments provide a method of modulating a TRPC6 function in a cell or animal comprising administering an effective amount of a compound that inhibits a TRPC6 function, wherein the compound inhibits a TRPC6-mediated ion flux. Certain embodiments provide a method of modulating a TRPC6 function in a cell or animal comprising administering an effective amount of a compound that inhibits a TRPC6 function, wherein the compound inhibits a TRPC6-mediated calcium influx. Certain embodiments provide a method of modulating a TRPC6 function in a cell or animal comprising administering an effective amount of a compound that inhibits a TRPC6 function, wherein the compound inhibits a TRPC6-mediated cytoskeletal reorganization or alteration in cell morphology. Certain embodiments provide a method of modulating a TRPC6 function in a cell comprising administering to the cell an effective amount of a compound that inhibits TRPC6 function, wherein the compound inhibits outward current mediated by TRPC6. Certain embodiments provide a method of modulating a TRPC6 function in a cell comprising administering to the cell an effective amount of a compound that inhibits TRPC6 function, wherein the compound inhibits inward current mediated by TRPC6. Certain embodiments provide a method of modulating a TRPC6 function in a cell comprising administering to the cell an effective amount of a compound that inhibits TRPC6 function, wherein the compound inhibits both the inward and outward currents mediated by TRPC6. Certain embodiments provide a method of modulating a TRPC6 function in a cell comprising administering to the cell an effective amount of a compound that inhibits TRPC6 function, wherein the compound inhibits TRPC6 mediated increases in intracellular calcium concentration. Certain embodiments provide a method of modulating a TRPC6 function in a cell comprising administering to the cell an effective amount of a compound that inhibits TRPC6 function, wherein the compound inhibits alterations in cell morphology. Certain embodiments also provide a method of preventing or treating a disease or condition related to TRPC6 function in a subject comprising administering to the subject a therapeutically effective amount of a compound that inhibits TRPC6 function, wherein the compound inhibits the inward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the outward current mediated by TRPC6. Certain embodiments also provide a method of preventing or treating a disease or condition related to TRPC6 function in a subject comprising administering to the subject a therapeutically effective amount of a compound that inhibits TRPC6 function, wherein the compound inhibits both the inward and outward current mediated by TRPC6. Certain embodiments provide a method of preventing or treating a disease or condition related to TRPC6 function in a subject comprising administering to the subject a therapeutically effective amount of a compound that inhibits TRPC6 function, wherein the compound inhibits the ion flux mediated by TRPC6. Note that inhibition of a particular current refers to the ability of a compound to inhibit that current (e.g., inward and/or outward) in either an in vitro or an in vivo assay. Inhibition of a particular current in either an in vivo or an in vitro assay serves as a proxy for the particular functional activity of the particular compound.

The present invention provides methods of treating a TRPC6 mediated disorder in a subject, the method comprising administering an effective amount of a compound of the invention wherein each of the variables above are described herein, for example, in the detailed description below.

The present invention further provides a method for treating a TRPC6 mediated disorder in a subject, wherein the method comprises administering a composition comprising a compound of the invention and a pharmaceutically acceptable excipient, diluent or carrier.

The present invention further provides a method for treating a TRPC6 mediated disorder in a subject, wherein the method comprises administering a composition comprising a compound of the invention and a pharmaceutically acceptable excipient, diluent or carrier, and the TRPC6 mediated disorder is selected from sepsis, severe sepsis, septic shock, cardiac hypertrophy, ischemia, ischemic reperfusion injury, hypertension, pulmonary arterial hypertension, idiopathic pulmonary arterial hypertension, restenosis, chronic obstructive pulmonary disease, cystic fibrosis, Alzheimer's disease, Parkinson's disease, Huntington's disease, amyotrophic lateral sclerosis (ALS), trauma induced brain disorders, asthma, disease, rheumatoid arthritis, osteoarthritis, inflammatory bowel disease, multiple sclerosis, muscular dystrophy, Duchenne's muscular dystrophy, preeclampsia and pregnancy-induced hypertension, non-alcoholic steatohepatitis, minimal change disease, focal segmental glomerulosclerosis (FSGS), nephrotic syndrome, diabetic nephropathy or diabetic kidney disease (DKD), chronic kidney disease, renal insufficiency, end stage renal disease, ischemia or an ischemic reperfusion injury, cancer, diabetes, lung fibrosis, idiopathic pulmonary fibrosis (IPF), emphysema and acute respiratory disease syndrome (ARDS)/severe acute respiratory syndrome (SARS).

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Some of the compounds in Table 1.1 can exist in more than one tautomeric form. The invention includes methods for using all such tautomers.

The invention includes pharmaceutically acceptable derivatives of compounds of the invention. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The compounds of the invention are only those which are contemplated to be "chemically stable" as will be appreciated by those skilled in the art. For example, a compound which would have a "dangling valency", or a "carbanion" are not compounds contemplated by the inventive methods disclosed herein.

List of Abbreviations

ACN or MeCN Acetonitrile
aq. Aqueous
BEH Ethylene Bridged Hybrid
Boc tert-Butyloxycarbonyl
° C. Degree celsius
CDI Di(imidazol-1-yl)methanone
CPhos-3G—Methanesulfonato(2-dicyclohexylphosphino-2',6'-bis(dimethylamino)-palladacycle methane 1,1'-biphenyl)(2'-amino-1,1'-biphenyl-2-yl)palladium(II) sulfonate
DCM Dichloromethane
DIPEA N,N-diisopropylethylamine
DMF N,N-dimethylformamide
DMA N,N-dimethylacetamide
DMSO Dimethylsulfoxide
DPPF 1,1'-Bis (diphenylphosphino) ferrocene
DTAD Di-tert-butyl azodicarboxylate
EDCl.HCl 1-Ethyl-3-(3-dimethylaminopropyl)carbodiimide hydrochloride
eq Equivalent
ESI-MS Electrospray ionisation mass spectrometry
$Et_2O$ Diethylether
EtOH Ethanol
EtOAc or EE Ethyl acetate
Grubbs $2^{nd}$ Gen. (1,3-Bis-(2,4,6-trimethylphenyl-2-imidazolidinylidene)-dichloro(phenylmethylene)(tricyclohexylphosphine)-ruthenium
h Hour
$H_2$ Hydrogen
HATU N,N,N',N'-tetramethyl-O-(7-azabenzotriazol-1-yl) uronium hexafluorophosphate
HCl Hydrochloric acid
HOBT 1-Hydroxybenzotriazole
HPLC High performance liquid chromatography
IPA Propan-2-ol
L Liter
$LiAlH_4$ Lithium aluminium hydride
LiHMDS Lithium bis(trimethylsilyl)amide
LiOH Lithium hydroxide
MeI Methyl iodide
MeOH Methanol
min Minute mL Milliliter
MS Mass spectrum
MTBE tert-Butyl methylether
m/z Mass-to-charge ratio
NaH Sodium hydride
NaOH Sodium hydroxide
$NH_3$ Ammonia
$NH_4OH$ Solution of $NH_3$ in water
NMP N-methyl-2-pyrrolidinone
n-BuOH 1-Butanol
$Pd_2(dba)_3$ Tris(dibenzylideneacetone)dipalladium(0)
Pd/C Palladium on carbon
$PdCl_2(dppf)CH_2Cl_2$ [1,1'-Bis(diphenylphosphino)ferrocene]dichloropalladium(II) dichloromethane
$PdCl_2(PPh_3)_2$ Bis(triphenylphosphine)palladium(II) chloride
$Pd(OH)_2$ Palladium hydroxide
PE Petroleum ether
RP Reversed phase
RT or rt Room temperature (about 20° C.)
$R_t$ Retention time
RuPhos Pd G3 (2-Dicyclohexylphosphino-2',6'-diisopropoxy-1,1'-biphenyl)[2-(2'-amino-1,1'-biphenyl)]palladium(II) methanesulfonate
$scCO_2$ Supercritical carbondioxide
SFC Supercritical fluid chromatography
TBAF Tetrabutylammonium fluoride
TBTU Benzotriazolyl tetramethyluronium tetrafluoroborate
TEA Triethylamine
TetrakisPd Tetrakis(triphenylphosphine)palladium(0)
TF or TFA Trifluoroacetic acid
THF Tetrahydrofuran
TLC Thin-layer chromatography on $SiO_2$
TPP Triphenylphosphine
XPhos 2-Dicyclohexylphosphino-2',4',6'-tri-i-propyl-1,1'-biphenyl
XPhos Pd G2 or Xphos Pd $2^{nd}$ Gen. Chloro(2-dicyclohexylphosphino-2',4',6'-thisopropyl-1,1'-biphenyl)[2-(2'-amino-1,1'-biphenyl)]palladium(II)
XantPhos 4,5-Bis(diphenylphosphino)-9,9-dimethylxanthene

SYNTHETIC EXAMPLES

The examples which follow are illustrative and, as recognized by one skilled in the art, particular reagents or conditions could be modified as needed for individual compounds without undue experimentation.

Intermediates and examples reported in the following bearing a basic or acidic group may be obtained as a corresponding salt or neutral compound depending on the purification method and conditions employed. Salts can be transformed into their neutral counterparts by standard procedures known to the one skilled in the art.

General Methods: Unless noted otherwise, all reactions are run at room temperature (about 25° C.), under inert atmosphere (e.g., Argon, $N_2$), and under anhydrous conditions. All compounds are characterized by at least one of the following methods: $^1$H NMR, HPLC, HPLC-MS, or melting point.

Typically, reaction progress is monitored by thin layer chromatography (TLC) or HPLC-MS. Intermediates and products are purified using at least one of the following methods:

Flash chromatography on silica gel, recrystallization, Super Critical Fluid (SCF) Chiral HPLC using a 10×250 mm or a 20×250 mm column, eluting with an isocratic mixture of MeOH with 20 mM $NH_3$, EtOH with 20 mM $NH_3$ or Isopropanol (IPA) with 20 mM $NH_3$, and super critical carbon dioxide at 150 bar; 60 up to 80 mL/min, and/or reversed phase HPLC using a C18 semi-preparative column eluting with a gradient of:

ACN and $H_2O$ and 0.1% TFA,
ACN and $H_2O$ and 0.1% $NH_3$ (aqueous),
ACN and $H_2O$+0.1% TFA,
ACN and $H_2O$+0.1% $NH_3$ (aqueous),
MeCN+0.1% TFA and $H_2O$+0.1% TFA,
MeCN+0.1% formic acid and $H_2O$+0.1% formic acid,
MeCN and $H_2O$ containing 2.5 mM $NH_4HCO_3$,
MeCN and $H_2O$+0.1% $NH_3$ (aqueous),
MeOH and $H_2O$+0.1% TFA,
MeCN+0.08% TFA and $H_2O$+0.1% TFA Analytical Data The reported mass spectrometry (MS) data is for observed mass (e.g., [M+H]$^+$). HPLC method used to characterize the compounds of the invention is described in Table 2.1 and Table 2.2.

Table 2.1: HPLC Methods

Method 1

| Method Name: | 1 | | | |
|---|---|---|---|---|
| Device description: | Agilent 1200 with DA- and MS-Detector | | | |
| Column: | Sunfire C18_3.0 × 30 mm_2.5 µm | | | |
| Column producer: | Waters | | | |

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method 2

| Method Name: | 2 | | | |
|---|---|---|---|---|
| Device description: | Agilent 1200 with DA- and MS-Detector | | | |
| Column: | Zorbax StableBond C18_3.0 × 30 mm_1.8 µm | | | |
| Column producer: | Agilent | | | |

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method 3

| Method Name: | 3 | | | |
|---|---|---|---|---|
| Device description: | Agilent 1200 with DA- and MS-Detector | | | |
| Column: | XBridge C18_3.0 × 30 mm_2.5 µm | | | |
| Column producer: | Waters | | | |

| Gradient/Solvent Time [min] | % Sol [Water 0.1% NH3] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Method 11

| | | Method Name: | 11 | | |
|---|---|---|---|---|---|
| | | Device description: | Waters Acquity, QDa Detector | | |
| | | Column: | Sunfire C18_3.0 × 30 mm_2.5 µm | | |
| | | Column producer: | Waters | | |

| Gradient/Solvent Time [min] | % Sol [Water 0.1% TFA (v/v)] | % Sol [Acetonitrile 0.08% TFA (v/v)] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Method E

| Method Name: | E |
|---|---|
| Device description: | Agilent 1260 SFC with DAD and ELSD |
| Column: | Lux ® Cellulose-4_4.6 × 250 mm_5 µm |
| Column producer: | Phenomenex |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Method T

| Method Name: | T |
|---|---|
| Device description: | Agilent 1260 SFC with DAD and MS |
| Column: | Chiralpak ® IG_4.6 × 250 mm_5 µm |
| Column producer: | Daicel |

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

NMR Method:

NMR spectra are recorded on a Bruker Advance 400 MHz or on a Bruker Avance 600 MHz using Bruker Topspin software. Chemical shifts are given in parts per million (ppm) downfield from internal reference trimethylsilane in δ units. Selected 1H-NMR data are reported in the following manner: chemical shift (multiplicity, coupling constants (J), number of hydrogens). Abbreviations are as follows: s (singulet), d (doublet), t (triplet), q (quartet), spt (septet), m (multiplet), br (broad).

General Methods

The compounds of the invention may be prepared by the general methods and examples presented below and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of invention.

Some of the intermediates described in the Synthetic Examples Section may be drawn for simplicity as free base, but according to the described reaction procedure those compounds may actually form a salt.

Intermediates and examples reported in the following bearing a basic or acidic group may be obtained as a corresponding salt or neutral compound depending on the purification method and conditions employed. Salts can be transformed into their neutral counterparts by standard procedures known to the one skilled in the art.

Preparation

The compounds according to the invention and their intermediates may be obtained using methods of synthesis which are known to one skilled in the art and described in the literature of organic synthesis. Preferably the compounds are obtained analogously to the methods of preparation explained in more detail hereinafter, in particular as described in the experimental section. In some cases the sequences adopted in carrying out the reaction schemes may be varied. Variants of these reactions, that are known to a person skilled in the art, but are not described in detail here may also be used. The general processes for preparing the compounds according to the invention will become apparent to a person skilled in the art by studying the schemes that follow. Starting compounds are commercially available or may be prepared by methods that are described in the literature or herein, or may be prepared in an analogous or similar manner. Before the reaction is carried out, any functional groups in the starting compounds may be protected using conventional protecting groups. These protecting groups may be cleaved again at a suitable stage within the reaction sequence using methods familiar to the skilled person and described in the literature for example in "Protecting Groups", $3^{rd}$ Edition, Philip J. Kocienski, Thieme, 2005 and "Protective Groups in Organic Synthesis", $4^{th}$ Edition, Peter G. M. Wuts, Theodora W. Greene, John Wiley & Sons, 2006.

As depicted in Scheme 1 the compounds of the general formula (I) of the invention may be prepared by the reaction of a suitable carboxylic acid of formula INT-1 (either as a free acid or as a salt with a suitable metal cation such as $Li^+$, $Na^+$, $K^+$, etc.) and a suitable amine intermediate of the general formula INT-2 (either as a free amine or as a salt such as hydrochloride, hydrobromide, etc.) in a suitable solvent (e.g. N,N-dimethylformamide, N,N-dimethylacetamide, 1-methyl-2-pyrrolidinone, dichloromethane, tetrahydrofuran, 1,4-dioxane, etc.) in the presence of a suitable coupling agent (e.g. O-(7-azabenzotriazol-1-yl)-N,N,N',N'-tetramethyluronium hexafluorophosphate (HATU), O-(benzotriazol-1-yl)-N,N—N',N'-tetramethyl-uronium tetrafluoroborate (TBTU), (benzotriazol-1-yloxy)tripyrrolidinophosphonium hexafluorophosphate (PyBOP), carbodiimide reagents, etc.) and a base (e.g. trimethylamine, N,N-diisopropyl-ethylamine, pyridine, etc.) to form an amide bond. The groups/terms $R^1$ to $R^5$, X and A in Scheme 1 have the meanings as defined hereinbefore and hereinafter.

The carboxylic acid INT-1 may alternatively be transformed into a carboxylic chloride (using e.g. thionyl chloride or oxalyl chloride in dichloromethane) and coupled as such with amine INT-2 in the presence of a suited base (e.g. trimethylamine, N,N-diisopropyl-ethylamine, pyridine, etc.) in an appropriate solvent. The groups/terms $R^1$ to $R^5$, X and A in Scheme 1 have the meanings as defined hereinbefore and hereinafter. Alternatively the carboxylic acid INT-1 can be activated with di(imidazole-1-yl)methanone (CDI) and coupled as such with an amine INT-2 in the presence of a suited base (e.g. trimethylamine, N,N-diisopropyl-ethylamine, etc.) in an appropriate solvent (e.g. N,N-dimethylformamide, N,N-dimethylacetamide, etc.). Intermediates INT-1 and INT-2 are known in the art or can be prepared by the methods described below or in the literature of organic chemistry.

Intermediate INT-2 may be used as a mixture of stereoisomers or as stereoisomeric pure compound. In case INT-2 is used as a stereoisomeric mixture, the resulting compounds of the general formula (I) may also be a mixture of stereoisomers. A mixture of stereoisomers of compound of the general formula (I) can be separated into stereoisomerically pure compounds by methods known to a person skilled in the art. The groups/terms $R^1$ to $R^5$, X and A in Scheme 1 have the meanings as defined hereinbefore and hereinafter.

The intermediates of the general formula INT-2 shown in Scheme 1 may be prepared according to Scheme 2. The group/term $R^1$ to $R^3$ and A in Scheme 2 have the meanings as defined hereinbefore and hereinafter.

Intermediate INT-5 may be prepared from boronic acid derivative INT-3 and a halogen containing heteroaromatic derivative INT-4. The reaction is performed with a palladium catalyst (e.g. 1,1'-bis(diphenylphosphino)-ferrocene]-dichloropalladium(II)-CH$_2$Cl$_2$-complex (PdCl$_2$(dppf) *CH$_2$Cl$_2$), or chloro(2-dicyclohexylphosphino-2',4',6'-triisopropyl-1,1'-biphenyl)[2-(2'-amino-1,1'-biphenyl)] palladium(II) (XPhos Pd 2$^{nd}$ generation catalyst), or tris (dibenzylideneacetone)-dipalladium Pd$_2$(dba)$_3$ with additional XPhos as ligand, etc.) in the presence of a base (e.g. potassium phosphate, sodium carbonate, etc.) in an appropriate solvent (water/tetrahydrofuran, water/1,4-dioxane, water/n-butanol, 1,4-dioxane or N,N-dimethylformamide, etc.) at elevated temperature e.g. 80° C. to 150° C. The reaction may optionally be performed in a microwave.

In case a heteroaromatic intermediate INT-4 is employed with a protected or masked amino group (NL$_2$ is not NH$_2$) this group can be transformed afterwards into the NH$_2$ group by cleaving off the protective group applying standard procedures reported in the literature of organic chemistry. A tert.-butyl carbonyl group (such as a Boc protecting group) is preferably cleaved under acidic conditions with e.g. trifluoroacetic acid or hydrochloric acid, in a solvent such as dichloromethane, 1,4-dioxane, isopropanol, HCl in 1,4-dioxane or ethyl acetate, etc. A benzyl group may be removed by using hydrogen in the presence of a transition metal such as palladium on carbon. Benzyl groups bearing electron donating groups such as methoxy on the aromatic ring may also be removed under acidic conditions (e.g. with trifluoroacetic acid or hydrochloric acid). The 2,5-dimethylpyrrol ring may be cleaved to release the amino-functionality by hydroxylamine hydrochloride and trimethylamine in an appropriate solvent like a mixture of ethanol and water at elevated temperature preferably 80 to 100° C.

The nitrogen-atom of the piperidine ring of the intermediate INT-3 may be protected with an appropriate protecting group PG1 (e.g. tert-butyl-oxycarbonyl (Boc), benzyl-oxycarbonyl (Cbz), benzyl (Bn), etc.). The protecting group PG1 can be introduced by methods known to a person skilled in the art. The removal of the protecting group PG1 from INT-6 yielding INT-2 as shown in Scheme 2 can be performed by methods known to a person skilled in the art or as described hereinbefore and hereinafter. Preferably a tert.-butyl carbonyl group (such as a Boc protecting group) can be cleaved under acidic conditions with e.g. trifluoroacetic acid or hydrochloric acid, in a solvent such as dichloromethane, 1,4-dioxane, isopropanol, HCl in 1,4-dioxane or ethyl acetate, etc. The group/term $R^1$ to $R^3$ and A in Scheme 2 have the meanings as defined hereinbefore and hereinafter.

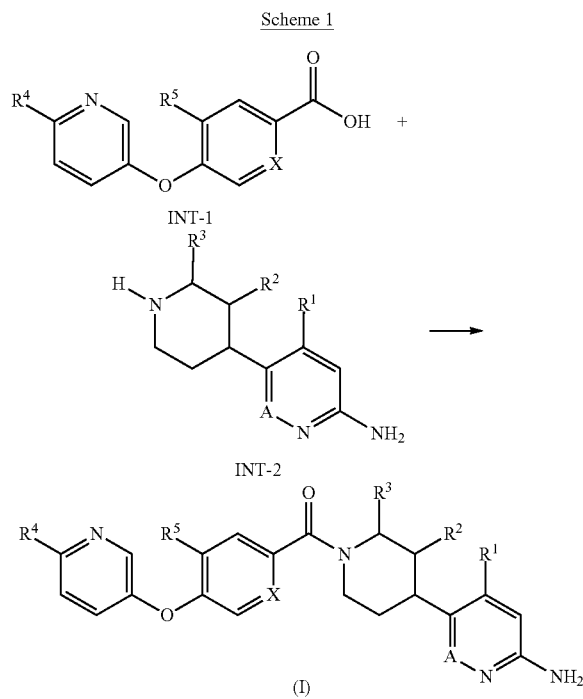

Scheme 1

Scheme 2

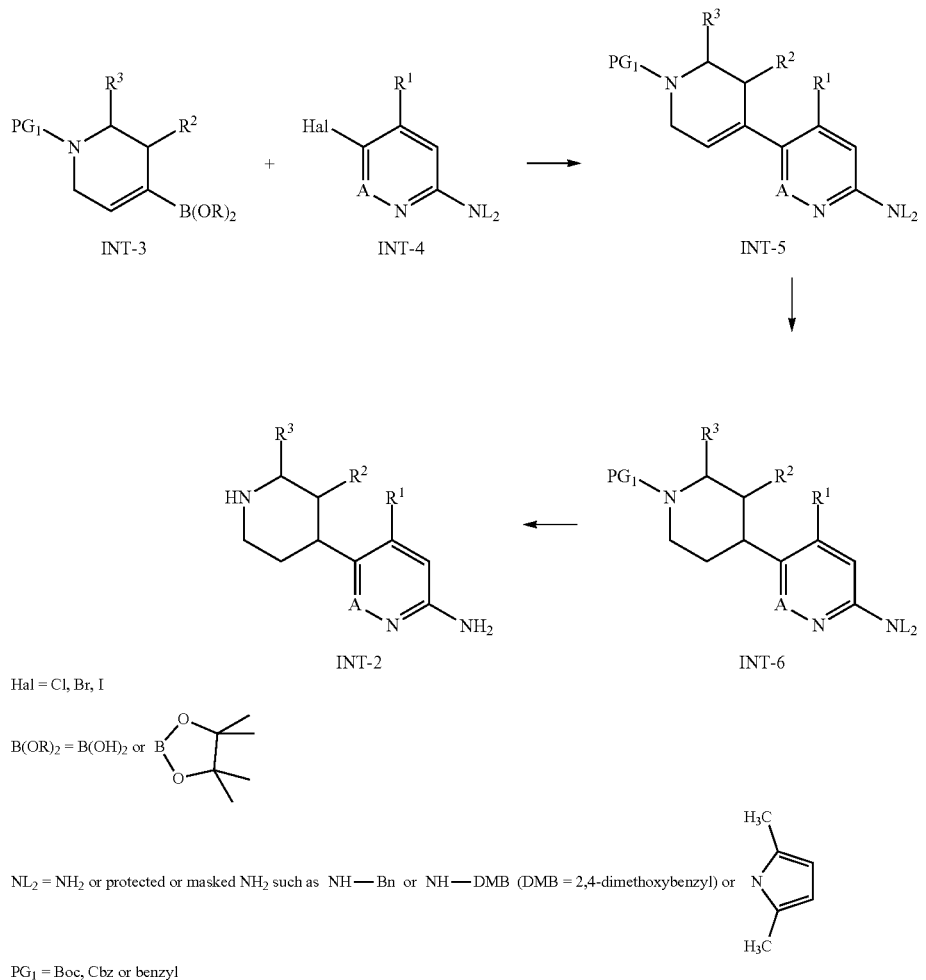

Hal = Cl, Br, I

B(OR)$_2$ = B(OH)$_2$ or 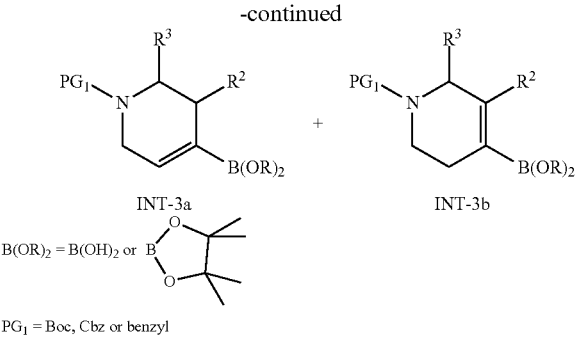

NL$_2$ = NH$_2$ or protected or masked NH$_2$ such as NH—Bn or NH—DMB (DMB = 2,4-dimethoxybenzyl) or PG$_1$ = Boc, Cbz or benzyl The position of the double bond in the tetrahydropyridine moiety of the intermediate INT-3 in Scheme 2 may depend on the reaction conditions which lead to the formation of INT-3 and/or on the exact substitution pattern of INT-3. For the sake of simplicity INT-3 may represent herinbefore and hereinafter as shown in Scheme 3 a mixture of INT-3a and INT-3b or represents either INT-3a or INT-3b. The terms $R^1$ to $R^3$, PG1 and B(OR)$_2$ have the meaning as shown in Scheme 2 or hereinbefore or hereinafter.

Scheme 3

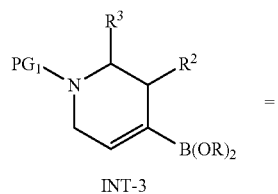

=

-continued

B(OR)$_2$ = B(OH)$_2$ or

PG$_1$ = Boc, Cbz or benzyl

The position of the double bond in the tetrahydropyridine moiety of the intermediate INT-5 may depend on the reaction conditions which lead to the formation of INT-5 and/or on the exact substitution pattern of INT-5. For the sake of simplicity INT-5 may represent herinbefore and hereinafter as shown in Scheme 4 a mixture of INT-5a and INT-5b or represents either INT-5a or INT-5b. The terms $R^1$ to $R^3$ A, PG$_1$ and NL$_2$ have the meaning as shown in Scheme 2 or hereinbefore or hereinafter.

Scheme 4

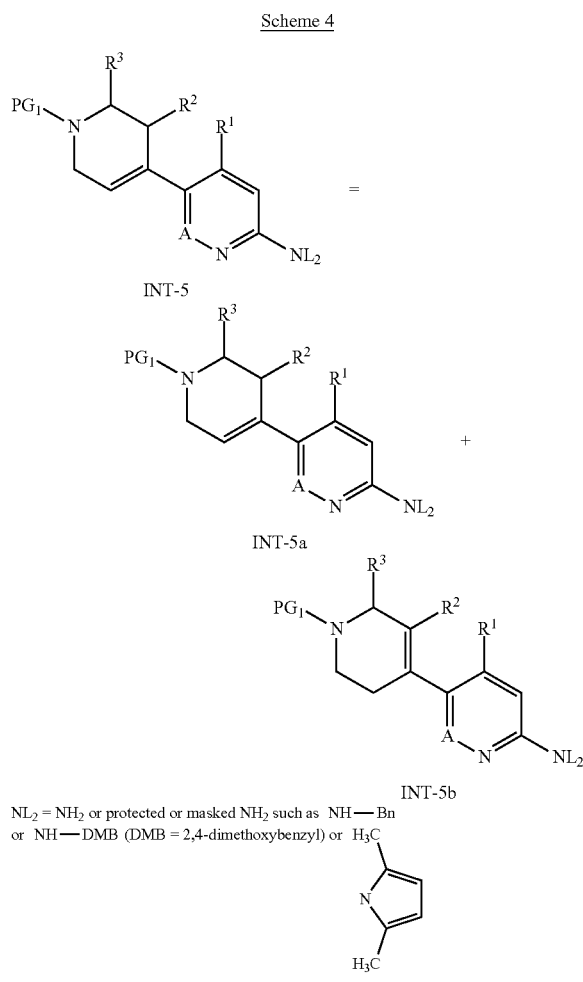

NL$_2$ = NH$_2$ or protected or masked NH$_2$ such as NH—Bn
or NH—DMB (DMB = 2,4-dimethoxybenzyl) or PG$_1$ = Boc, Cbz or benzyl As shown in Scheme 2 the double bond in the tetrahydropyridine moiety of intermediate INT-5 may be hydrogenated by using hydrogen in the presence of a transition metal, preferably palladium (or Pd(OH)$_2$, etc.) on carbon in a solvent such as methanol, ethanol, tetrahydrofuran, 1,4-dioxane, methanol/acetic acid, etc. to yield INT-6. Preferably, hydrogen is applied at 1 to 5 bar pressure and the reaction may be performed at room temperature up to 50° C.

As shown in Scheme 2 the hydrogenation of the intermediate INT-5 may lead to the generation of a stereocenter depending on R$^2$ and R$^3$. INT-6 may be a mixture of stereoisomers. Those mixtures of stereoisomers may be separated into the stereochemically pure compounds of INT-6 by methods known to a person skilled in the art. Alternatively, a mixture of stereoisomers of INT-6 may be taken to the next step resulting in a mixture of stereoisomers of INT-2. The mixture of stereoisomers of INT-2 may be separated into stereochemically pure compounds of the general formula INT-2 by methods known to a person skilled in the art. Alternatively a mixture of stereoisomers of INT-2 may be taken forward to the next step as shown in Scheme 1.

Depending on the reaction conditions and the overall deprotection strategy (removal of the protecting group PG1 from INT-6 and conversion of NL$_2$ to NH$_2$) the intermediate INT-2 may be obtained in Scheme 2 either as a free base or as a salt such as hydrochloride, trifluoroacetate, hydrobromide, etc. The salt of the intermediate INT-2 may be transformed into their neutral counterparts by standard procedures known to the one skilled in the art.

As shown in Scheme 5 intermediate INT-7 may be attached to INT-8 via an oxygen starting from various precursors. The two parts (INT-7 and the aromatic/heteroaromatic moiety of INT-8) may be linked using one of them decorated with a hydroxyl group (V or W denoted OH) and the other one with a boronic acid derivative (e.g. W or V denoted B(OH)$_2$, B(OCMe$_2$CMe$_2$O), etc.). The two building blocks INT-7 and INT-8 accordingly equipped may be coupled employing copper(acetate) in the presence of a base (e.g. pyridine or trimethylamine), molecular sieves, optionally a co-oxidant (e.g. oxygen), in a solvent, e.g. dichloromethane, at 0 to 60° C. The groups/terms V, W, X, PG$_2$, R$^4$ to R$^5$ in Scheme 5 have the meanings as defined hereinbefore and hereinafter.

Alternatively, the linkage between INT-7 and INT-8 via oxygen is formed upon coupling INT-7 bearing an OH group (V=OH) and the pyridine moiety of INT-8, bearing a leaving group (W=e.g. F, Cl, Br). The oxygen of the OH group of INT-7 replaces the leaving group by nucleophilic substitution or a transition metal catalyzed reaction. INT-8 is coupled with the hydroxylated INT-7 in the presence of a base (e.g. Cs$_2$CO$_3$, K$_2$CO$_3$, KOH, trimethylamine or NaH) preferably in a solvent (e.g. toluene, tetrahydrofuran, 1,2-dimethoxyethane, 1,4-dioxane, N,N-dimethylformamide, N,N-dimethylacetamide, N-methylpyrrolidinone, alcohol, water or mixtures thereof), at 0 to 220° C.

As shown in Scheme 5 carboxylic acids of formula INT-1, wherein the group/term X, R$^4$ to R$^5$ have the meanings as defined hereinbefore and hereinafter, are preferably prepared from the corresponding ester of the general formula INT-9 by hydrolysis or hydrogenolysis depending on the nature of the protecting group PG2. The ester group of INT-9 may be hydrolyzed in the presence of an acid such as hydrochloric acid or sulfuric acid, or an alkali metal hydroxide such as lithium hydroxide, sodium hydroxide or potassium hydroxide to yield the carboxylic acid. The hydrolysis is preferably conducted in aqueous solvents, such as water combined with tetrahydrofuran, 1,4-dioxane, alcohol (e.g. methanol, ethanol and isopropanol), or dimethyl sulfoxide at 0 to 120° C. If the protecting group PG2 of INT-9 represents lower alkyl group esters such as ethyl or methyl esters, those are preferably cleaved by hydrolysis with a hydroxide base such as NaOH, LiOH or KOH in a mixture of water and a suitable miscible solvent (e.g. tetrahydrofuran, methanol, ethanol, 1,4-dioxane, etc. or mixtures of these), with heating if necessary. The tert.-butyl ester is preferably cleaved by treatment under acidic conditions (e.g. hydrochloric acid or trifluoroacetic acid) in a suitable solvent (e.g. dichloromethane, 1,4-dioxane, methanol, ethanol, tetrahydrofuran, water or mixtures of these). A benzyl ester is preferably cleaved using hydrogen in the presence of a transition metal (preferably e.g. palladium on carbon, etc.) in a suitable solvent (e.g. ethanol, methanol, tetrahydrofuran, dichloromethane, ethyl acetate) under an atmosphere of hydrogen (preferably 1 to 5 bar). Benzyl esters bearing electron donating groups on the phenyl ring, such as methoxy, may also be removed under oxidative conditions, e.g. ceric ammonium nitrate (CAN) or 2,3-dichloro-5,6-dicyanoquinone (DDQ) are reagents commonly used for this approach. The acid INT-1 in Scheme 5 may be isolated either as a salt with the metal cation or as a free acid depending on the reaction conditions.

Scheme 5

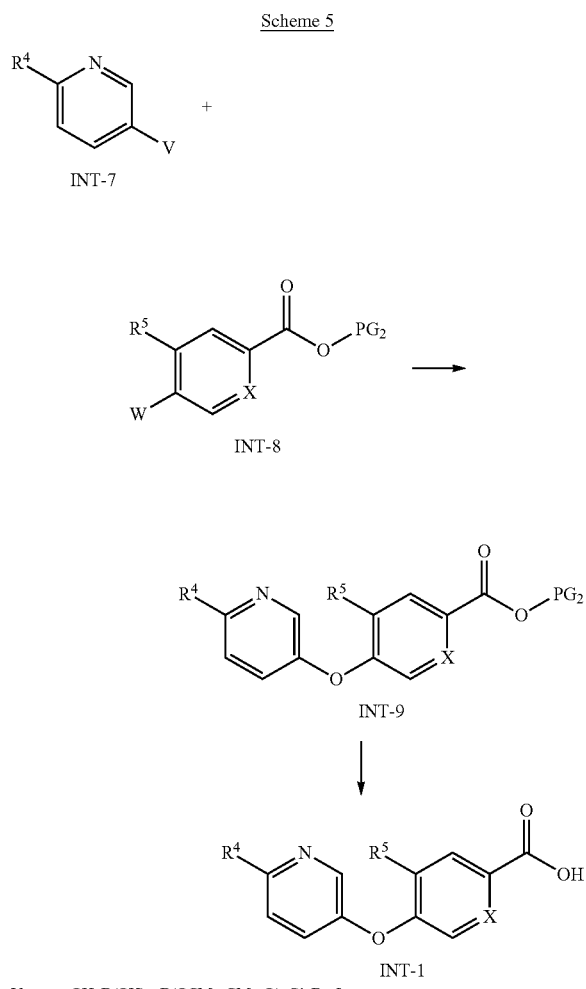

V = e.g., OH, B(OH)$_2$, B(OCMe$_2$CMe$_2$O), Cl, Br, I
W = e.g., OH, B(OH)$_2$, B(OCMe$_2$CMe$_2$O), F, Cl, Br, I
PG$_2$ = Methyl, ethyl, tert.-butyl, benzyl Carboxylic acids of formula INT-1, wherein the group/term X, $R^4$ to $R^5$ have the meanings as defined hereinbefore and hereinafter can be synthesized according to Scheme 6. The intermediate INT-12 may be synthesized, upon coupling the hetaryl moiety INT-10 bearing an OH group and INT-11, bearing a leaving group (W=e.g. F, Cl, Br). The oxygen of the OH group of INT-10 replaces the leaving group by nucleophilic substitution or a transition metal catalyzed reaction to provide INT-12. INT-10 is coupled with INT-11 in the presence of a base (e.g. 052003, K$_2$CO$_3$, KOH, trimethylamine or NaH) preferably in a solvent (e.g. toluene, tetrahydrofuran, 1,2-dimethoxyethane, 1,4-dioxane, N,N-dimethylformamide, N,N-dimethylacetamide, N-methylpyrrolidinone, dimethylsulfoxide, alcohol, water or mixtures thereof), at 0 to 220° C. The cyano group of INT-12 can be converted into the corresponding carboxylic group according to methods known to a person skilled in the art leading to the acid of the general formula INT-1. Preferably the cyano-group of INT-12 is treated with sodium hydroxide in a solvent such as water, methanol, ethanol, or mixtures hereof at elevated temperatures at 20 to 120° C. to yield the corresponding carboxylic acid INT-1. The group/term W, X and $R^4$ to $R^5$ have the meanings as defined hereinbefore and hereinafter or as defined in scheme 6.

Scheme 6

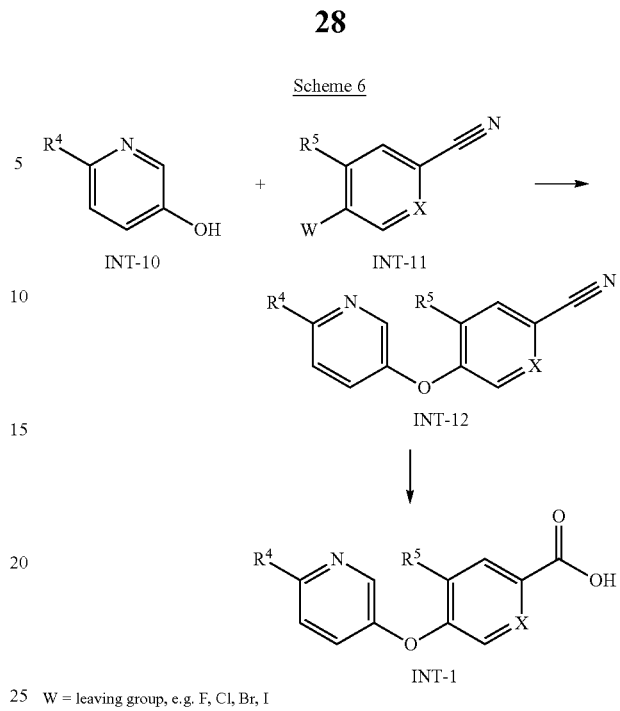

W = leaving group, e.g. F, Cl, Br, I

The synthetic routes presented may rely on the use of protecting groups. For example, potentially reactive groups present, such as hydroxyl, carbonyl, carboxyl, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

To obtain the compounds of the general formula I stereochemical mixtures may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optical active solvent or by reacting with an optically active substance which forms salts or derivatives such as esters or amides with the racemic compound. Salts may be formed with enantiomerically pure acids for basic compounds and with enantiomerically pure bases for acidic compounds.

Diastereomeric derivatives are formed with enantiomerically pure auxiliary compounds, e.g. acids, and their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose, as well as optically active alcohols applicable as auxiliary residues, are known to those skilled in the art.

SYNTHETIC EXAMPLES

Synthesis of Intermediates

Intermediate 1.1 tert-Butyl (6S)-6-methyl-4-(trifluoromethanesulfonyloxy)-1,2,3,6-tetrahydropyridine-1-carboxylate and tert-butyl (2S)-2-methyl-4-(trifluoromethanesulfonyloxy)-1,2,3,6-tetrahydropyridine-1-carboxylate

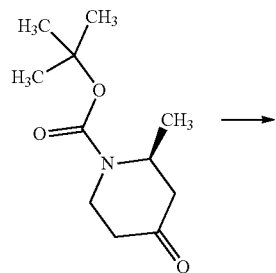

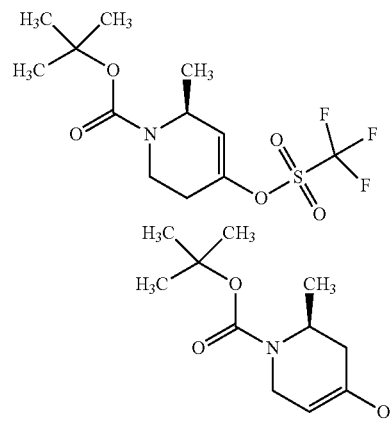

The reaction is performed under an argon atmosphere. tert-Butyl (2S)-2-methyl-4-oxopiperidine-1-carboxylate (3.00 g; 14.07 mmol) in THF (50 mL) is cooled to −70° C. LiHMDS (1 mol/L in THF; 19.69 mL; 19.69 mmol) is added dropwise. After stirring for 1 hour at −70° C. 1,1,1-trifluoro-N-phenyl-N-trifluoromethanesulfonylmethanesulfonamide (6.03 g; 16.88 mmol) is added. The reaction mixture is allowed to stir 30 minutes at −70° C. and 3 hours at 0° C. The reaction mixture is diluted with DCM and washed with NaOH (1 mol/L; aq. solution). The organic layer is dried over $Na_2SO_4$, filtered and concentrated under reduced pressure. The residue is used without further purification.

Yield: 5.0 g (quantitative)

Intermediate 1.2 tert-Butyl (6S)-4-(6-amino-4-methylpyridazin-3-yl)-6-methyl-1,2,3,6-tetrahydropyridine-1-carboxylate and tert-butyl (2S)-4-(6-amino-4-methylpyridazin-3-yl)-2-methyl-1,2,3,6-tetrahydropyridine-1-carboxylate

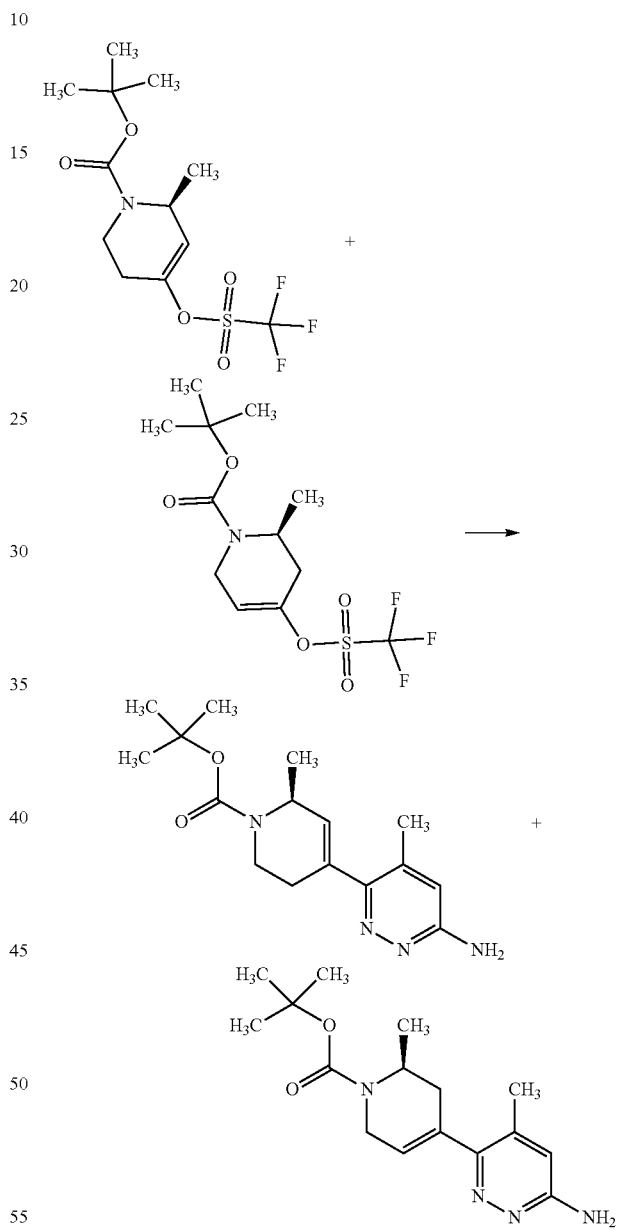

A mixture of tert-Butyl (6S)-6-methyl-4-(trifluoromethanesulfonyloxy)-1,2,3,6-tetrahydropyridine-1-carboxylate and tert-butyl (2S)-2-methyl-4-(trifluoromethanesulfonyloxy)-1,2,3,6-tetrahydropyridine-1-carboxylate (4.00 g; 11.58 mmol), 4,4,5,5-tetramethyl-2-(4,4,5,5-tetramethyl-1,3,2-dioxaborolan-2-yl)-1,3,2-dioxaborolane (3.36 g; 13.24 mmol), Xphos (0.55 g; 1.16 mmol), Xphos Pd 2nd generation catalyst (0.46 g; 0.58 mmol) and potassium acetate (3.87 g; 39.38 mmol) in EtOH (75 mL) are purged with argon and stirred at 90° C. for 1.5 hours. 6-Chloro-5-methylpyridazin- 3-amine (1.66 g; 11.58 mmol) and sodium carbonate (2 mol/L; aq. solution; 20.85 mL; 41.70 mmol) are added and the reaction mixture is stirred at reflux for 4 hours. The reaction mixture is concentrated under reduced pressure. The residue is taken up in water and extracted several times with EtOAc. The combined organic layers are washed with water, dried over $Na_2SO_4$, filtered and concentrated under reduced pressure. The residue is taken up in MeOH, filtered and concentrated under reduced pressure. The remaining residue is purified by silica gel chromatography (DCM/MeOH).

Yield: 1.8 g (51%) $R_t$(H PLC): 0.83 min (method 1)

Intermediate 1.3 and Intermediate 1.4 tert-Butyl (2S,4S)-4-(6-amino-4-methylpyridazin-3-yl)-2-methylpiperidine-1-carboxylate and tert-butyl (2S,4R)-4-(6-amino-4-methylpyridazin-3-yl)-2-methylpiperidine-1-carboxylate

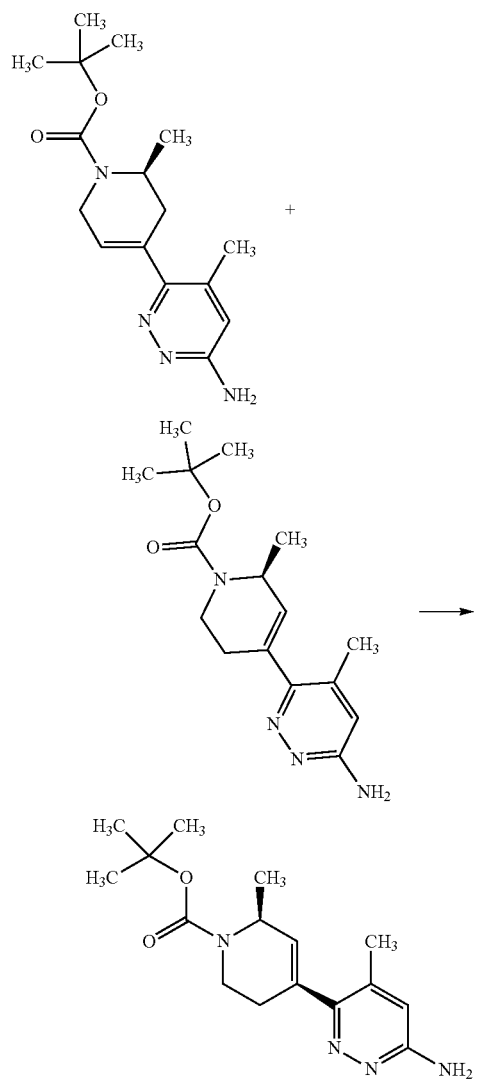

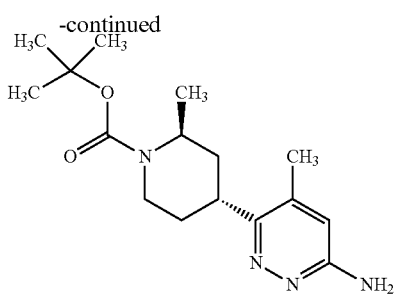

Under a hydrogen atmosphere (Parr-apparatus; 3 bar) a mixture of tert-Butyl (6S)-4-(6-amino-4-methylpyridazin-3-yl)-6-methyl-1,2,3,6-tetrahydropyridine-1-carboxylate and tert-butyl (2S)-4-(6-amino-4-methylpyridazin-3-yl)-2-methyl-1,2,3,6-tetrahydropyridine-1-carboxylate (1.8 g, 5.91 mmol) and Pd/C (10%; 0.25 g) in MeOH (30 mL) are stirred at RT for 23 hours. Additional catalyst is added and further hydrogenated for additional 21 h at RT at 3 bar hydrogen atmosphere. After removal of the catalyst by filtration the mother liquid is concentrated under reduced pressure and purified by silica gel chromatography (DCM/MeOH) to obtain a mixture of diastereomers. The diastereomers are separated by chiral HPLC (Chiralpak® IG 20×250 mm, 5 µM; $scCO_2$/MeOH+20 mM $NH_3$ 75%/25%, 150 bar, 40° C., 60 mL/min).

Intermediate 1.3: tert-Butyl (2S,4S)-4-(6-amino-4-methylpyridazin-3-yl)-2-methylpiperidine-1-carboxylate: Yield: 0.46 g (25%) ESI-MS: m/z=307 [M+H]$^+$ $R_t$(HPLC): 2.99 min (method T)

Intermediate 1.4: tert-Butyl (2S,4R)-4-(6-amino-4-methylpyridazin-3-yl)-2-methylpiperidine-1-carboxylate: Yield: 0.66 g (36%) ESI-MS: m/z=307 [M+H]$^+$ $R_t$(HPLC): 4.10 min (method T)

Intermediate 1.5

5-Methyl-6-[(2S,4S)-2-methylpiperidin-4-yl]pyridazin-3-amine tert-Butyl (2S,4S)-4-(6-amino-4-methylpyridazin-3-yl)-2-methylpiperidine-1-carboxylate (0.45 g; 1.47 mmol) and TFA (20%; solution in DCM; 10.0 mL) are stirred at RT for 2 hours. The reaction mixture is concentrated under reduced pressure and purified by RP-HPLC (ACN/water/NH₄OH, column: xbridge). The residue is taken up in diethyl ether and concentrated under reduced pressure.

Yield: 0.30 g (99%) ESI-MS: m/z=207 [M+H]⁺
R_f(HPLC): 0.68 min (method 3)

Intermediate 1.6

5-Methyl-6-[(2S,4S)-2-methylpiperidin-4-yl]pyridazin-3-amine dihydrobromide

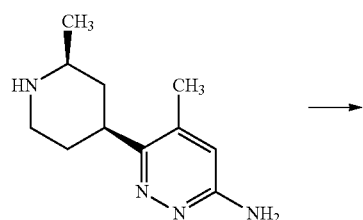

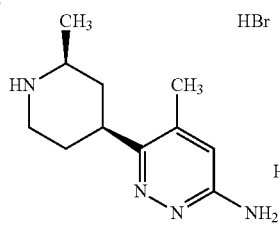

In a vial 5-methyl-6-[(2S,4S)-2-methylpiperidin-4-yl]pyridazin-3-amine (35 mg, 0.17 mmol) is taken up with MeOH (280 µL) and HBr (48% in water, 38 µL, 0.34 mmol) is added. The vial is closed and the reaction mixture is stirred for 1 h at 50° C. The stirring is switched off and the reaction mixture is cooled with 0.4° C./min to RT. The reaction mixture is left at RT without stirring over night. The reaction mixture is heated to 50° C. with 0.4° C./min without stirring and cooled to 25° C. with 0.4° C./min twice and left at RT without stirring for 5 days. The formed crystal is analysed by Xray crystallography to determine the absolute stereochemistry.

Intermediate 1.7

5-Methyl-6-[(2S,4R)-2-methylpiperidin-4-yl]pyridazin-3-amine dihydrochloride

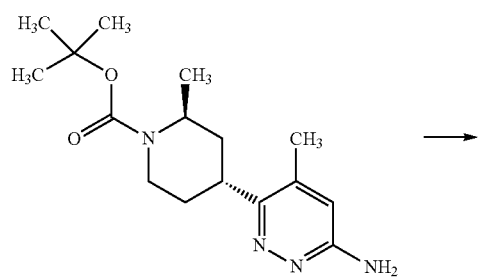

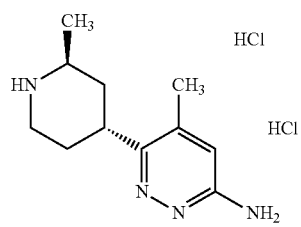

tert-Butyl (2S,4R)-4-(6-amino-4-methylpyridazin-3-yl)-2-methylpiperidine-1-carboxylate (1.20 g; 3.92 mmol) and TFA (20%; solution in DCM; 20.0 mL) are stirred at RT for 2 hours. The reaction mixture is concentrated under reduced pressure and purified by RP-HPLC (ACN/water/NH₄OH, column xbridge). The residue is taken up in HCl (1.25 mol/L; solution in MeOH) and concentrated under reduced pressure.

Yield: 0.80 g (73%) ESI-MS: m/z=207 [M+H]⁺
R_f(HPLC): 0.69 min (method 3)

Intermediate 2.1 tert-Butyl 3-methyl-4-(trifluoromethanesulfonyloxy)-1,2,3,6-tetrahydropyridine-1-carboxylate

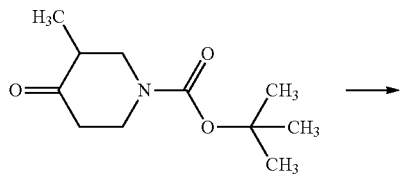

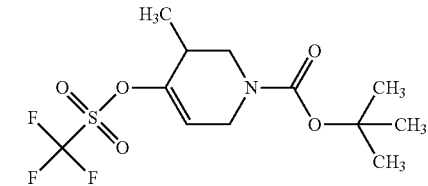

The reaction is performed under an argon atmosphere. tert-Butyl 3-methyl-4-oxopiperidine-1-carboxylate (10.0 g; 46.9 mmol) in THF (170 mL) is cooled to −70° C. LiHMDS (1 mol/L; solution in THF; 65.6 mL; 65.6 mmol) is added dropwise. After stirring for 1 hour at −70° C. 1,1,1-trifluoro-N-phenyl-N-trifluoromethanesulfonylmethanesulfonamide (20.1 g; 56.3 mmol) in THF (50 mL) is added dropwise. The reaction mixture is stirred for 1 hour at −70° C. and 3 hours at 0° C. After stirring at RT over night the reaction mixture is diluted with water and extracted several times with EtOAc. The combined organic layers are dried with Na₂SO₄, filtered and concentrated under reduced pressure. The residue is used without further purification.

Yield: 16 g (99%) ESI-MS: m/z=290 [M+H-tert.-Butyl]⁺
R_f(HPLC): 1.21 min (method 3)

Intermediate 2.2 tert-Butyl 3-methyl-4-(4,4,5,5-tetramethyl-1,3,2-dioxaborolan-2-yl)-1,2,3,6-tetrahydropyridine-1-carboxylate

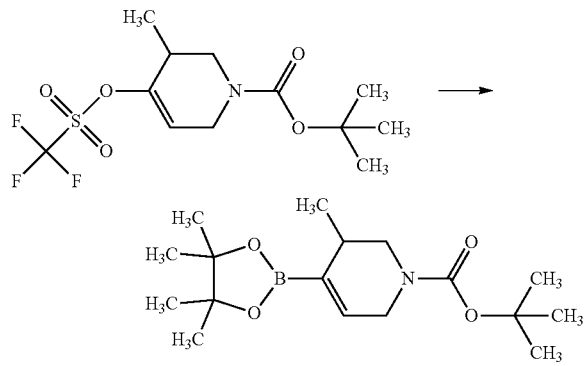

The reaction is performed under an argon atmosphere. tert-Butyl 3-methyl-4-(trifluoromethanesulfonyloxy)-1,2,3,6-tetrahydropyridine-1-carboxylate (16.0 g; 46.3 mmol) and 4,4,5,5-tetramethyl-2-(4,4,5,5-tetramethyl-1,3,2-dioxaborolan-2-yl)-1,3,2-dioxaborolane (13.5 g; 52.9 mmol), potassium acetate (15.5 g; 157.5 mmol) and Xphos (2.2 g; 4.6 mmol) are stirred in EtOH (300 mL). Xphos palladium 2$^{nd}$ generation catalyst (1.8 g; 2.3 mmol) are added. After stirring over night at 80° C. the reaction mixture is concentrated under reduced pressure. The residue is taken up in DCM, filtered and evaporated under reduced pressure. The residue is used without further purification.

Yield: 15.0 g (quantitative) ESI-MS: m/z=268 [M+H-tert.-butyl]$^{+}$ R$_t$(HPLC): 1.22 min (method 3)

Intermediate 2.3 tert-Butyl 4-(6-amino-4-methylpyridazin-3-yl)-3-methyl-1,2,3,6-tetrahydropyridine-1-carboxylate

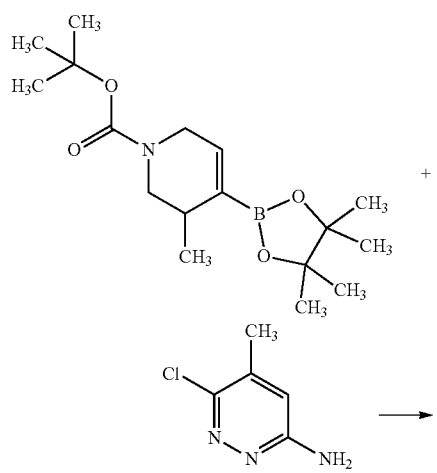

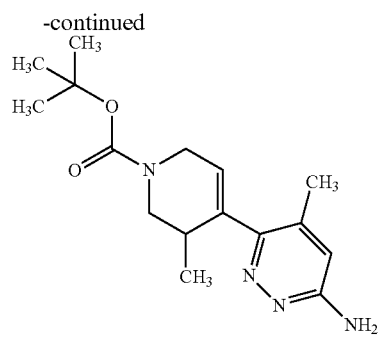

The reaction is performed under an argon atmosphere. tert-Butyl 3-methyl-4-(4,4,5,5-tetramethyl-1,3,2-dioxaborolan-2-yl)-1,2,3,6-tetrahydropyridine-1-carboxylate (15.00 g; 46.41 mmol), 6-chloro-5-methylpyridazin-3-amine (8.00 g; 55.69 mmol), potassium phosphate (34.48 g; 162.42 mmol) and palladium (0) tetrakis(triphenylphosphine) (5.36 g; 4.64 mmol) are stirred in 1,4-dioxane/water (300 mL/50 mL). After stirring at 100° C. over night the reaction mixture is filtered and concentrated under reduced pressure. The residue is taken up in EtOAc and water. The aqueous layer is extracted several times with EtOAc. The combined organic layers are dried over Na$_2$SO$_4$, filtered and concentrated under reduced pressure. The residue is purified by silica gel chromatography (EtOAC/MeOH).

Yield: 8.30 g (59%) ESI-MS: m/z=305 [M+H]$^{+}$ R$_t$(HPLC): 0.90 min (method 3)

Intermediate 2.4 tert-Butyl 4-(6-amino-4-methylpyridazin-3-yl)-3-methylpiperidine-1-carboxylate

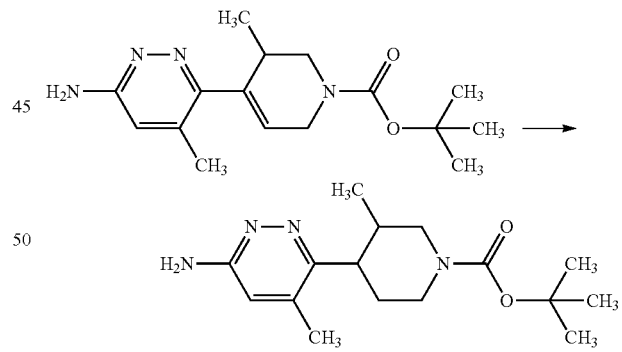

Under a hydrogen atmosphere (Parr-apparatus; 50 psi) tert-butyl 4-(6-amino-4-methylpyridazin-3-yl)-3-methyl-1,2,3,6-tetrahydropyridine-1-carboxylate (8.30 g; 27.27 mmol) and Pd/C (10%; 0.85 g) in MeOH (250 mL) are stirred at 40° C. in total for 70 hours. Additional catalyst is added after 19 h, 42 h and 67 h and further hydrogenated. After removal of the catalyst by filtration the mother liquid is concentrated under reduced pressure. The residue is used without further purification.

Yield: 8.30 g (99%) ESI-MS: m/z=307 [M+H]$^{+}$ R$_t$(HPLC): 0.90 min (method 3)

Intermediate 2.5 to Intermediate 2.8 tert-Butyl (3R,4S)-4-(6-amino-4-methylpyridazin-3-yl)-3-methylpiperidine-1-carboxylate and tert-butyl (3S,4R)-4-(6-amino-4-methylpyridazin-3-yl)-3-methylpiperidine-1-carboxylate and tert-butyl (3S,4S)-4-(6-amino-4-methylpyridazin-3-yl)-3-methylpiperidine-1-carboxylate and tert-butyl (3R,4R)-4-(6-amino-4-methylpyridazin-3-yl)-3-methylpiperidine-1-carboxylate

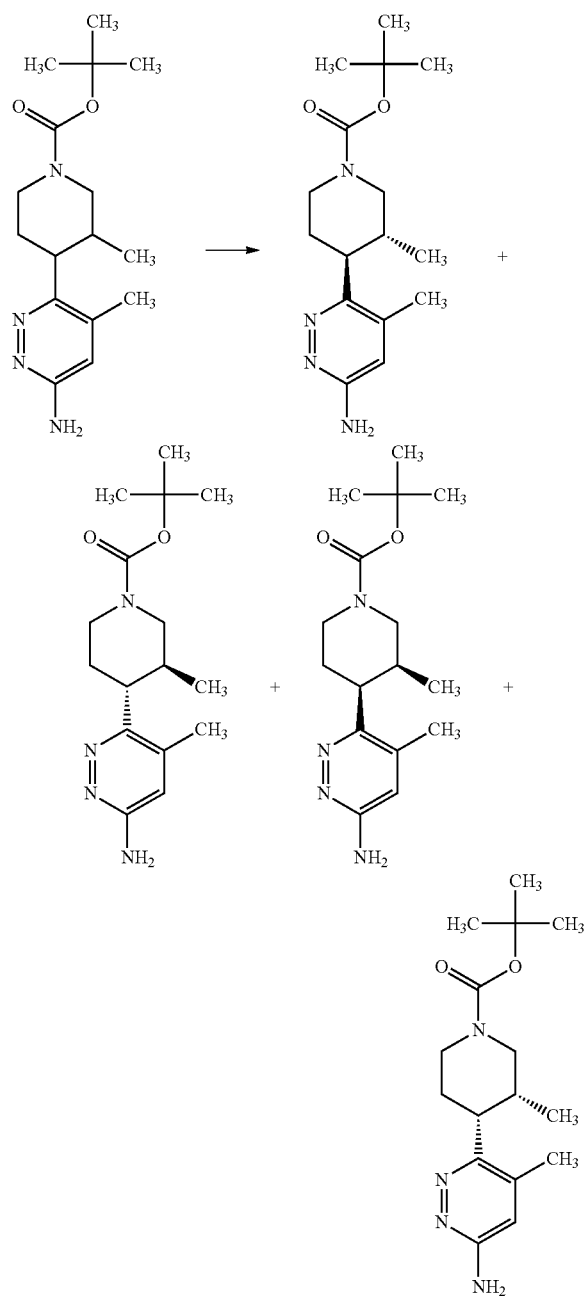

tert-Butyl 4-(6-amino-4-methylpyridazin-3-yl)-3-methylpiperidine-1-carboxylate (8.40 g; 27.41 mmol) is separated by chiral RP-HPLC (Lux® Cellulose-4, 21.2×250 mm, 5 μm; scCO$_2$/MeOH+20 mM NH$_3$ 75%/25%, 40° C., back-pressure 150 bar, flowrate 60 mL/min, temperature 40° C.).

The relative stereochemistry of the separated isomers is determined by NMR and the absolute stereochemistry of intermediate 5.7 and intermediate 5.8 is determined by X-ray.

Intermediate 2.5: first eluting trans diastereoisomer tert-butyl (3R,4S)-4-(6-amino-4-methylpyridazin-3-yl)-3-methylpiperidine-1-carboxylate: Yield: 0.52 g (6%) ESI-MS: m/z=307 [M+H]$^+$ R$_t$(HPLC): 3.63 min (method E)

Intermediate 2.6: second eluting trans diastereoisomer tert-Butyl (3S,4R)-4-(6-amino-4-methylpyridazin-3-yl)-3-methylpiperidine-1-carboxylate: Yield: 0.55 g (7%) ESI-MS: m/z=307 [M+H]$^+$ R$_t$(HPLC): 4.01 min (method E)

Intermediate 2.7: first eluting cis diastereoisomer: tert-butyl (3S,4S)-4-(6-amino-4-methylpyridazin-3-yl)-3-methylpiperidine-1-carboxylate): Yield: 2.35 g (28%) ESI-MS: m/z=307 [M+H]$^+$ R$_t$(HPLC): 4.66 min (method E)

Intermediate 2.8: second eluting cis diastereoisomer: tert-butyl (3R,4R)-4-(6-amino-4-methylpyridazin-3-yl)-3-methylpiperidine-1-carboxylate): Yield: 2.38 g (28%) ESI-MS: m/z=307 [M+H]$^+$ R$_t$(HPLC): 6.23 min (method E)

Intermediate 2.9

5-Methyl-6-[(3R,4R)-3-methylpiperidin-4-yl]pyridazin-3-amine dihydochloride

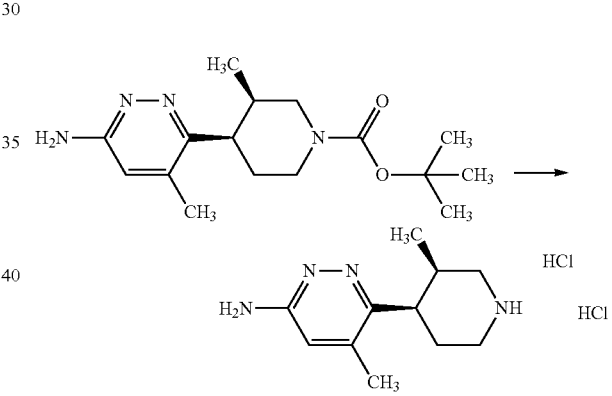

tert-Butyl (3R,4R)-4-(6-amino-4-methylpyridazin-3-yl)-3-methylpiperidine-1-carboxylate (intermediate 2.8, 2.10 g; 6.85 mmol) and HCl (4 mol/L; solution in 1,4-dioxane; 3.00 mL; 12.00 mmol) in DCM/MeOH (10 mL/1 mL) are stirred at RT for 1 hour. The reaction mixture is concentrated under reduced pressure.

Yield: 1.81 g (95%) ESI-MS: m/z=207 [M+H]$^+$ R$_t$(HPLC): 0.62 min (method 3)

5-Methyl-6-[(3R,4R)-3-methylpiperidin-4-yl]pyridazin-3-amine

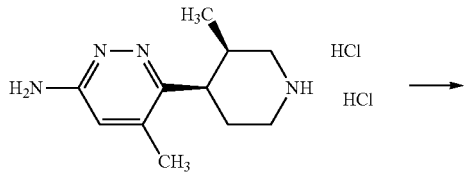

-continued

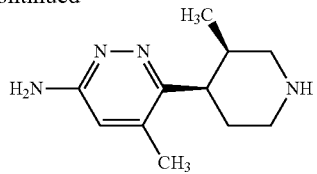

5-Methyl-6-[(3R,4R)-3-methylpiperidin-4-yl]pyridazin-3-amine dihydochloride (0.26 g; 0.93 mmol) is dissolved in MeOH and purified by RP-HPLC (ACN/water+NH$_3$, column: XBridge) several times.

Yield: 0.13 g (68%) ESI-MS: m/z=207 [M+H]$^+$

5-Methyl-6-[(3R,4R)-3-methylpiperidin-4-yl]pyridazin-3-amine dihydochloride

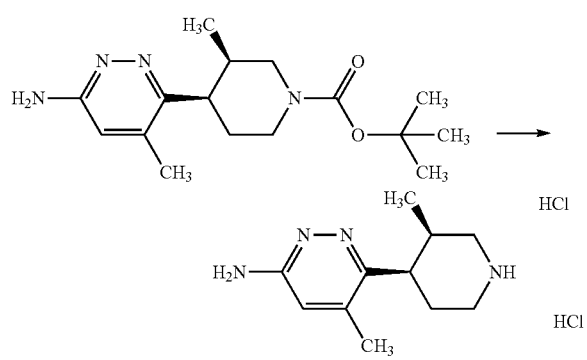

In a vial 5-methyl-6-[(3R,4R)-3-methylpiperidin-4-yl]pyridazin-3-amine (30.0 mg; 0.15 mmol) is stirred in MeOH (150 µL) and HCl (4 mol/L; solution in 1,4-dioxane; 73 µL; 0.29 mmol) is added. The vial is closed and heated to 50° C. with 5° C./min. The reaction mixture is left for 1 h at 50° C. and afterwards cooled with 1° C./min to RT without stirring. The reaction mixture is left at RT for 25 days. The formed crystal is analysed by Xray crystallography to determine the absolute stereochemistry.

Intermediate 2.10

5-Methyl-6-[(3S,4S)-3-methylpiperidin-4-yl]pyridazin-3-amine dihydochloride

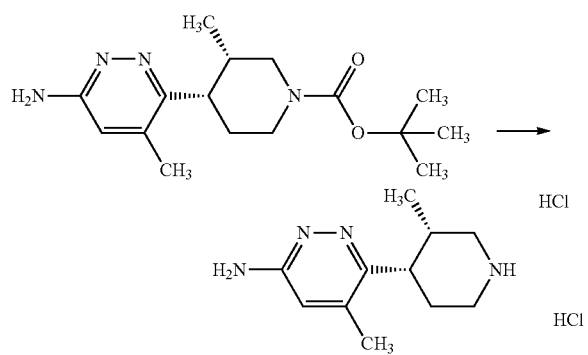

tert-Butyl (3S,4S)-4-(6-amino-4-methylpyridazin-3-yl)-3-methylpiperidine-1-carboxylate (intermediate 2.7, 2.07 g; 6.76 mmol) and HCl (4 mol/L; solution in 1,4-dioxane; 15.00 mL; 60.00 mmol) in DCM/MeOH (30 mL/10 mL) are stirred at RT for 1 hour. The reaction mixture is concentrated under reduced pressure.

Yield: quantitative ESI-MS: m/z=207 [M+H]$^+$ R$_t$(HPLC): 0.62 min (method 3)

5-Methyl-6-[(3S,4S)-3-methylpiperidin-4-yl]pyridazin-3-amine

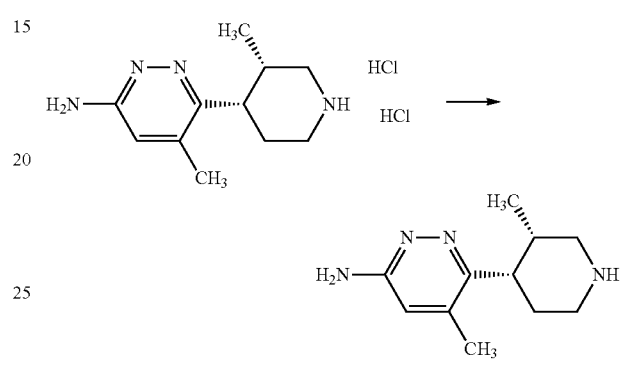

5-Methyl-6-[(3S,4S)-3-methylpiperidin-4-yl]pyridazin-3-amine dihydochloride (1.90 g; 6.81 mmol) is taken up in MeOH and set to a basic pH using NaOH (4 mol/L; aq. solution). The reaction mixture is purified by RP-HPLC (ACN/water+NH$_3$ column: XBridge).

Yield: 1.40 g (100%) ESI-MS: m/z=207 [M+H]$^+$ R$_t$(HPLC): 0.62 min (method 3)

5-Methyl-6-[(3S,4S)-3-methylpiperidin-4-yl]pyridazin-3-amine dihydrochloride

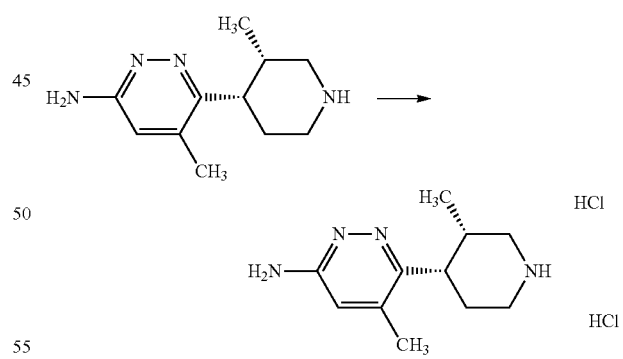

In a vial 5-methyl-6-[(3S,4S)-3-methylpiperidin-4-yl]pyridazin-3-amine (30.0 mg; 0.15 mmol) is stirred in MeOH (150 µL) and HCl (4 mol/L; solution in 1,4-dioxane; 73 µL; 0.29 mmol) is added and stirred at RT. The reaction mixture is heated to 50° C. with 5° C./min. The reaction mixture is stirred 90 min at 50° C. and afterwards cooled with 0.5° C./min to RT without stirring. The reaction mixture is left at RT over night without stirring. The formed crystals are analysed by Xray crystallography to determine the absolute stereochemistry.

Intermediate 2.11

5-Methyl-6-[(3R,4S)-3-methylpiperidin-4-yl]pyridazin-3-amine dihydochloride

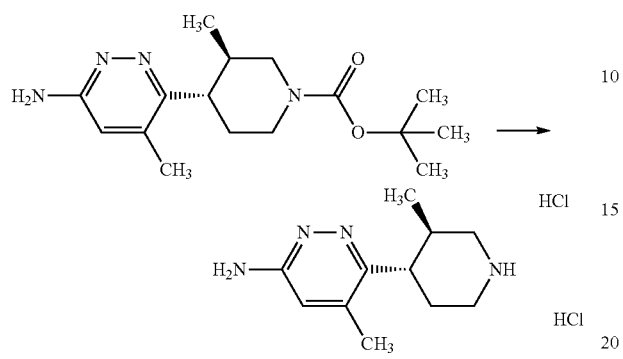

The first eluting trans diastereoisomer (intermediate 2.5) from the chiral separation of intermediate 2.4. (tert-Butyl (3R,4S)-4-(6-amino-4-methylpyridazin-3-yl)-3-methylpiperidine-1-carboxylate) (0.45 g; 1.47 mmol) and HCl (4 mol/L; solution in 1,4-dioxane; 1.50 mL; 6.00 mmol) in DCM/MeOH (5 mL/1 mL) are stirred at RT for 1 hour. The reaction mixture is concentrated under reduced pressure.

Yield: quantitative ESI-MS: m/z=207 [M+H]$^+$ R$_t$(HPLC): 0.66 min (method 3)

Intermediate 2.12

5-Methyl-6-[(3S,4R)-3-methylpiperidin-4-yl]pyridazin-3-amine dihydochloride

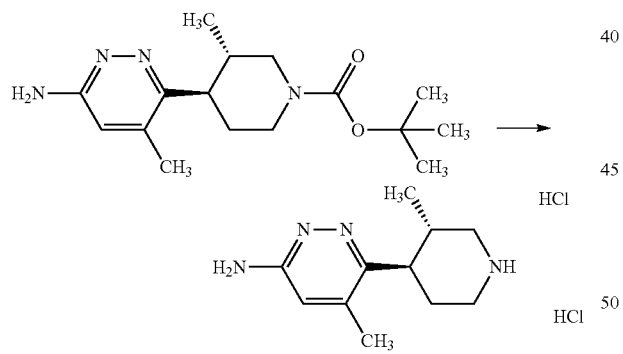

The second eluting trans diastereoisomer (intermediate 2.6) from the chiral separation of intermediate 2.4. (tert-Butyl (3S,4R)-4-(6-amino-4-methylpyridazin-3-yl)-3-methylpiperidine-1-carboxylate) (0.48 g; 1.58 mmol) and HCl (4 mol/L; solution in 1,4-dioxane; 1.50 mL; 6.00 mmol) in DCM/MeOH (5 mL/2 mL) are stirred at RT for 1 hour. The reaction mixture is concentrated under reduced pressure.

Yield: quantitative ESI-MS: m/z=207 [M+H]$^+$ R$_t$(HPLC): 0.66 min (method 3)

Analog as described for intermediate 2.9, 5-Methyl-6-[(3S,4R)-3-methylpiperidin-4-yl]pyridazin-3-amine dihydochloride is purified by RP-HPLC (ACN/water/NH$_3$) to obtain 5-methyl-6-[(3S,4R)-3-methylpiperidin-4-yl]pyridazin-3-amine. In a vial 5-methyl-6-[(3S,4R)-3-methylpiperidin-4-yl]pyridazin-3-amine (30.0 mg; 0.15 mmol) is stirred in MeOH (150 µL) and HCl (4 mol/L; solution in 1,4-dioxane; 73 µL; 0.29 mmol) is added. The vial is sealed and the reaction mixture is heated to 50° C. The reaction mixture is left 90 min at 50° C. Afterwards the cap is opened and the reaction mixture is left at RT over night without stirring. The formed crystals are analysed by Xray crystallography to determine the absolute stereochemistry.

Intermediate 3.1 tert-butyl 4-(6-aminopyridazin-3-yl)-1,2,3,6-tetrahydropyridine-1-carboxylate

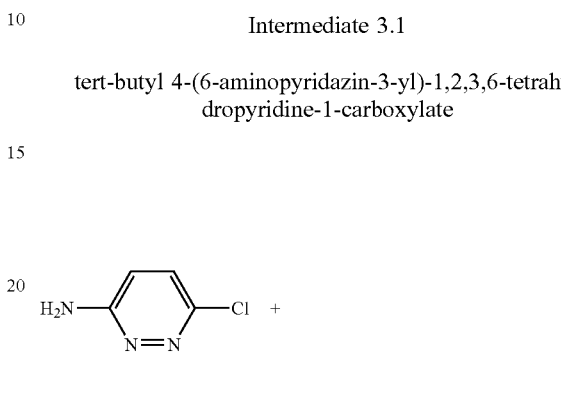

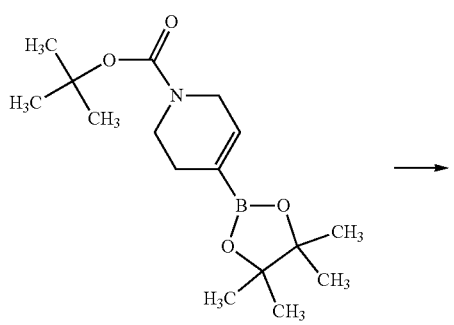

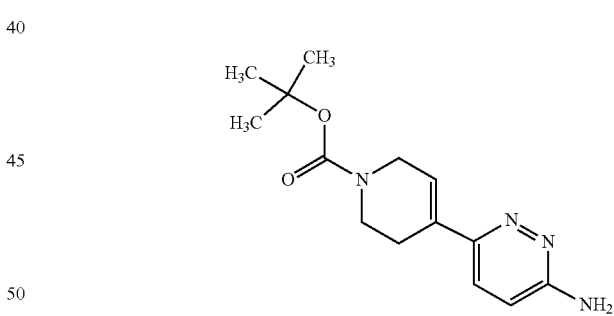

The reaction is performed using an argon-atmosphere. 6-Chloropyridazin-3-amine (5.20 g; 40.14 mmol), tert-butyl 4-(4,4,5,5-tetramethyl-1,3,2-dioxaborolan-2-yl)-1,2,3,6-tetrahydropyridine-1-carboxylate (13.65 g; 44.15 mmol) and sodium carbonate (2 mol/L; aq. solution; 80.28 mL; 160.56 mmol) in 1,4-dioxane (350 mL) is purged with argon. After 5 minutes Xphos Pd 2$^{nd}$ generation catalyst (0.95 g; 1.20 mmol) is added and the mixture is stirred over night at 100° C. The reaction mixture is filtered and concentrated under reduced pressure. The residue is taken up in MeOH, precipitated with water and filtered. The precipitate is dried in a drying oven at 50° C. The product is used without further purification.

Yield: quantitative ESI-MS: m/z=277 [M+H]$^+$ R$_t$(HPLC): 0.78 min (method 2)

Intermediate 3.2 tert-Butyl 4-(6-aminopyridazin-3-yl)piperidine-1-carboxylate

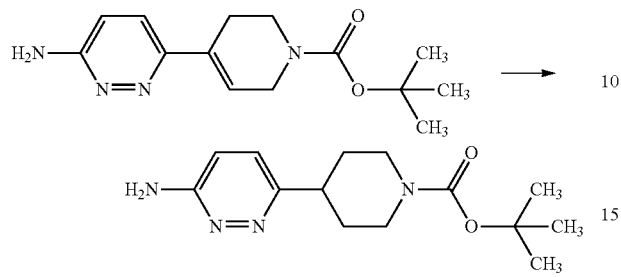

Under a hydrogen atmosphere (Parr-apparatus; 50 psi) tert-butyl 4-(6-aminopyridazin-3-yl)-1,2,3,6-tetrahydropyridine-1-carboxylate (12.0 g; 43.43 mmol) and Pd/C (10%; 1.0 g) in MeOH (250 mL) are stirred at RT for 20 hours. After removal of the catalyst by filtration the mother liquid is concentrated under reduced pressure. The product is purified by silica chromatography (DCM/MeOH).

Yield: 9.1 g (75%) ESI-MS: m/z=279 [M+H]$^+$ R$_t$(HPLC): 0.86 (method 3)

Intermediate 3.3

6-(Piperidin-4-yl)pyridazin-3-amine dihydrochloride

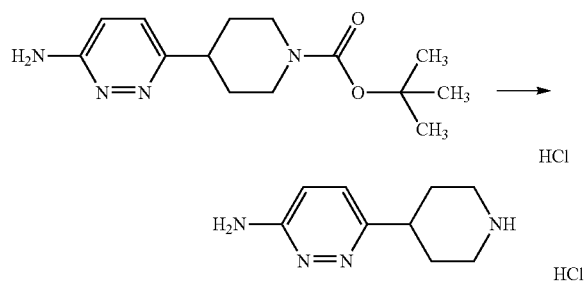

tert-Butyl 4-(6-aminopyridazin-3-yl)piperidine-1-carboxylate (1.00 g; 3.59 mmol) and HCl (4 mol/L; solution in 1,4-dioxane; 2.96 mL; 11.84 mmol) in ACN (6 mL) are stirred 40° C. for 2 hours. The precipitate is filtered and washed with isopropylacetate The solid material is dried.

Yield: 0.35 g (39%) ESI-MS: m/z=179 [M+H]$^+$ R$_t$(HPLC): 0.28 min (method 3)

Intermediate 4.1 tert-Butyl 4-(6-amino-4-methylpyridazin-3-yl)-1,2,3,6-tetrahydropyridine-1-carboxylate

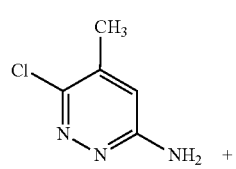 +

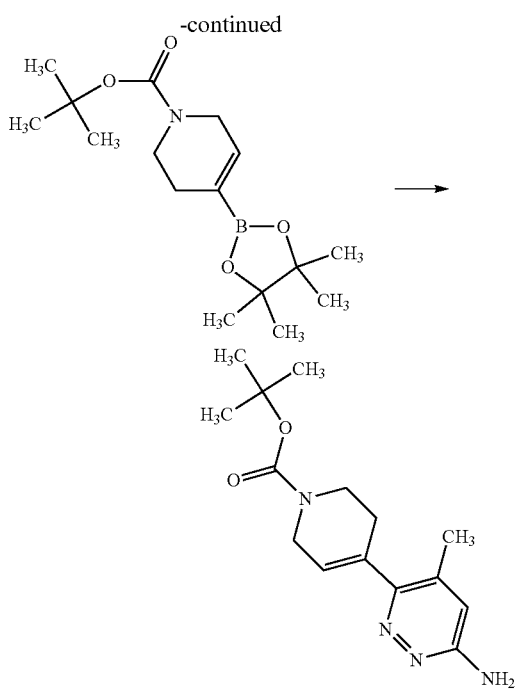

The reaction is performed using an argon-atmosphere. 6-Chloro-5-methylpyridazin-3-amine (3.00 g; 20.90 mmol), tert-butyl 4-(4,4,5,5-tetramethyl-1,3,2-dioxaborolan-2-yl)-1,2,3,6-tetrahydropyridine-1-carboxylate (7.11 g; 22.98 mmol) and sodium carbonate (2 mol/L; aq. solution; 41.79 mL; 83.58 mmol) in 1,4-dioxane (150 mL) are purged with argon. Xphos Pd 2$^{nd}$ generation catalyst (0.49 g; 0.63 mmol) is added and the mixture is stirred over night at 100° C. The organic solvent is evaporated and water and EtOAc is added. The aqueous layer is extracted several times with EtOAc. The combined organic layers are washed with brine. The organic layer is separated, dried over Na$_2$SO$_4$, filtered and concentrated under reduced pressure. The residue is purified by silica gel chromatography (DCM/MeOH).

Yield: 5.20 g (86%) ESI-MS: m/z=291 [M+H]$^+$ R$_t$(HPLC): 0.79 min (method 2)

Intermediate 4.2 tert-Butyl 4-(6-amino-4-methylpyridazin-3-yl)piperidine-1-carboxylate

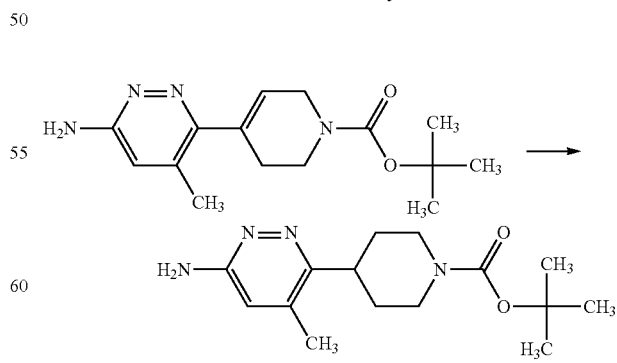

Under a hydrogen atmosphere (Parr-apparatus; 50 psi) tert-butyl 4-(6-amino-4-methylpyridazin-3-yl)-1,2,3,6-tetrahydropyridine-1-carboxylate (5.20 g; 17.91 mmol) and Pd/C (10%; 0.75 g) in MeOH (100 mL) are stirred at RT for 17 hours. After removal of the catalyst by filtration the mother liquid is concentrated under reduced pressure. The product is used without further purification.

Yield: 5.00 g (96%) ESI-MS: m/z=293 [M+H]+ $R_t$(HPLC): 0.79 (method 2)

Intermediate 4.3

5-Methyl-6-(piperidin-4-yl)pyridazin-3-amine bistrifluoroacetic acid

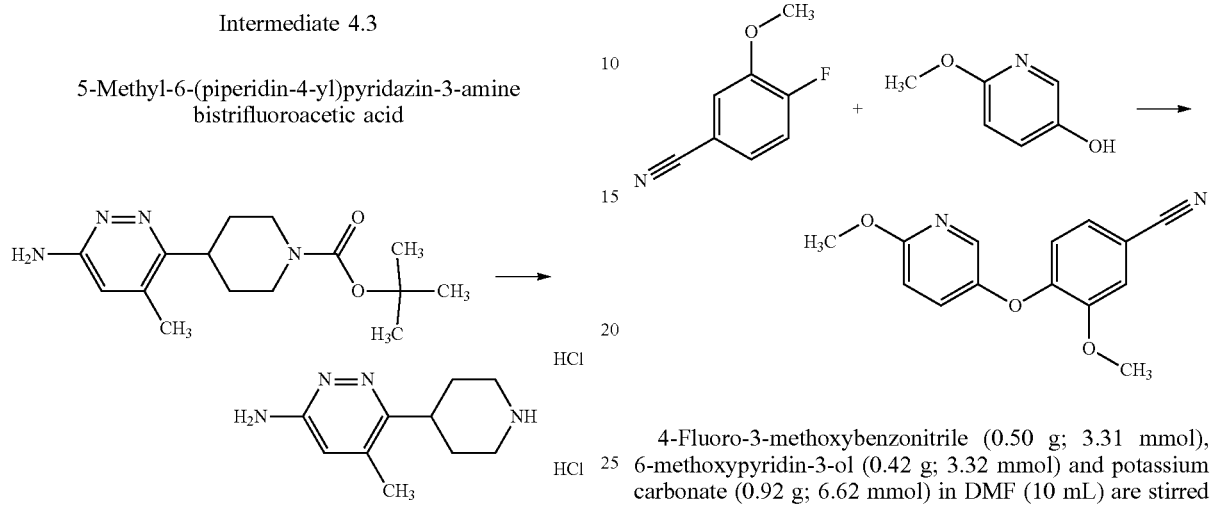

tert-Butyl 4-(6-amino-4-methylpyridazin-3-yl)piperidine-1-carboxylate (0.5 g; 1.71 mmol) and HCl (4 mol/L solution in 1,4-dioxane, 7.5 mL, 30.0 mmol) in 1,4-dioxane (3.5 mL) are stirred at RT over night. The reaction mixture is concentrated under reduced pressure and triturated with EtOAc. The residue is collected and dried.

Yield: 0.46 g (quantitative) ESI-MS: m/z=193 [M+H]+ $R_t$(HPLC): 0.61 (method 3)

Intermediate 5

4-[(6-Methoxypyridin-3-yl)oxy]benzoic acid

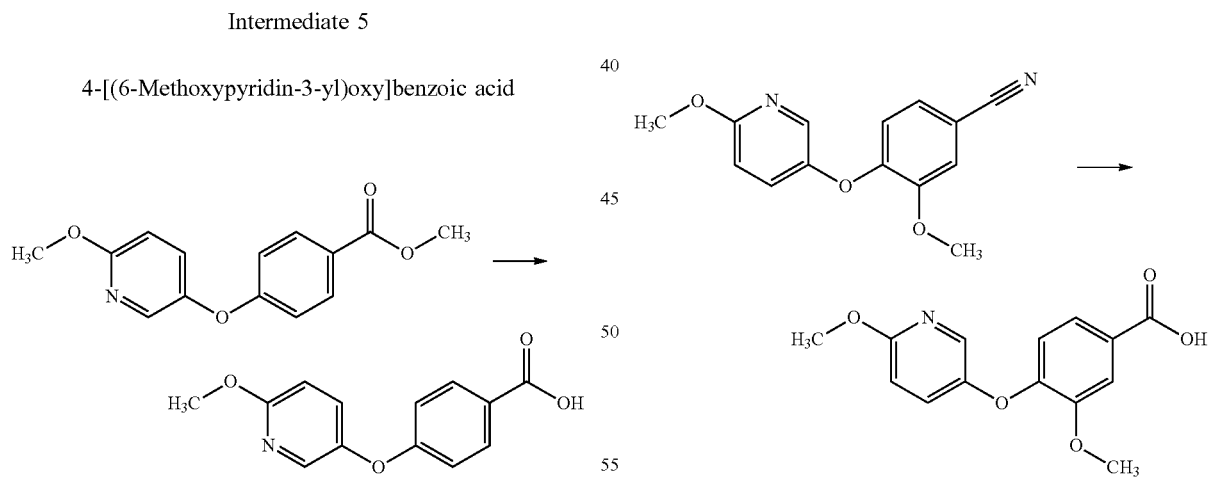

Methyl 4-[(6-methoxypyridin-3-yl)oxy]benzoate (0.27 g; 1.06 mmol) and NaOH (4 mol/L; aq. solution; 0.53 mL; 2.11 mmol) in MeOH (5 mL) is stirred at RT over night. The reaction is not complete, so additional NaOH (4 mol/L; aq. solution; 0.30 mL) is added and stirred for 3 hours. The reaction mixture is diluted with water and neutralized using HCl (4 mol/L; aq. solution). The resulting precipitate is filtered off and dried in a drying oven at 45° C.

Yield: 0.26 g (100%) ESI-MS: m/z=246 [M+H]+ $R_t$(HPLC): 0.59 (method 3)

Intermediate 6.1

3-Methoxy-4-[(6-methoxypyridin-3-yl)oxy]benzonitrile

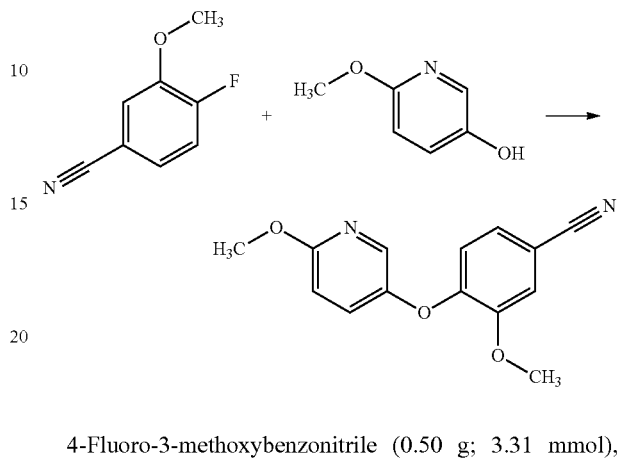

4-Fluoro-3-methoxybenzonitrile (0.50 g; 3.31 mmol), 6-methoxypyridin-3-ol (0.42 g; 3.32 mmol) and potassium carbonate (0.92 g; 6.62 mmol) in DMF (10 mL) are stirred at 100° C. over night. The reaction mixture is filtered and the mother liquid is purified by RP-HPLC (ACN/water+TFA, column: SunFire).

Yield: 0.12 g (14%) ESI-MS: m/z=257 [M+H]+ $R_t$(HPLC): 1.00 (method 1)

Intermediate 6.2

3-Methoxy-4-[(6-methoxypyridin-3-yl)oxy]benzoic acid

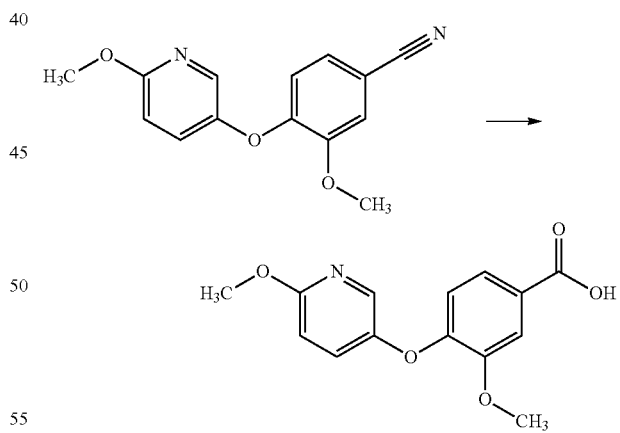

3-Methoxy-4-[(6-methoxypyridin-3-yl)oxy]benzonitrile (0.12 g; 0.47 mmol) and NaOH (1 mol/L; aq. solution; 3.00 mL; 3.00 mmol) are stirred at 100° C. for 4 hours. After cooling to RT the reaction mixture is diluted with water and acidified to ~pH 2 using HCl (1 mol/L; aq. solution). The aqueous layer is extracted several times with EtOAc. The combined organic layers are washed with water, dried over $Na_2SO_4$, filtered and concentrated under reduced pressure.

Yield: 0.12 g (93%) ESI-MS: m/z=276 [M+H]+ $R_t$(HPLC): 0.90 (method 1)

Intermediate 7.1

5-Fluoro-4-methoxypyridine-2-carbonitrile

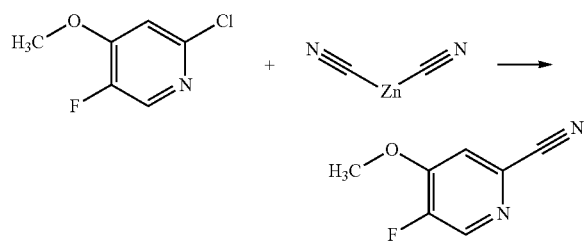

The reaction is performed under a nitrogen atmosphere. 2-Chloro-5-fluoro-4-methoxypyridine (500.0 mg; 3.10 mmol), zinc cyanide (365.0 mg; 3.11 mmol) and dppf (170.0 mg; 0.31 mmol) in DMF (10 mL) are purged with nitrogen. $Pd_2(dba)_3$ (280.0 mg; 0.31 mmol) is added. After stirring for 3 hours at 150° C. and over night at RT the reaction mixture is poured on $NaHCO_3$ (aq. solution; half-saturated) and extracted several times with EtOAc. The combined organic layers are washed with water and aqueous $NaHCO_3$ solution. The organic layers are dried over $Na_2SO_4$, filtered and concentrated under reduced pressure. The residue is purified with RP-HPLC (ACN/water+TFA, column: SunFire).

Yield: 120.0 mg (26%) ESI-MS: m/z=153 [M+H]$^+$ $R_t$(HPLC): 0.76 min (method 1)

Intermediate 7.2

4-Methoxy-5-[(6-methoxypyridin-3-yl)oxy]pyridine-2-carbonitrile

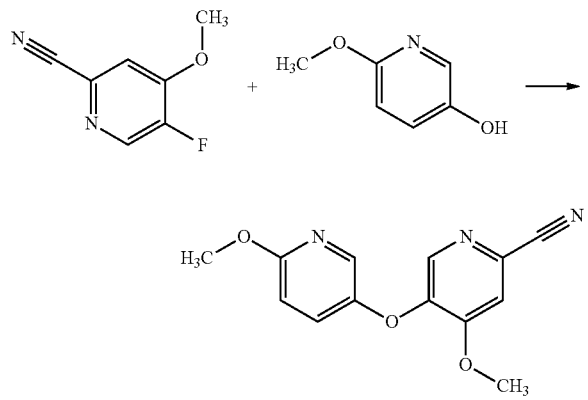

5-Fluoro-4-methoxypyridine-2-carbonitrile (0.50 g; 3.29 mmol), 6-methoxypyridin-3-ol (0.42 g; 3.32 mmol) and potassium carbonate (0.92 g; 6.62 mmol) in DMF (10 mL) are stirred at 100° C. over night. The reaction mixture is filtered and concentrated under reduced pressure. The residue is used without further purification.

Yield: quantitative ESI-MS: m/z=258 [M+H]$^+$ $R_t$(HPLC): 0.93 (method 1)

Intermediate 7.3

4-Methoxy-5-[(6-methoxypyridin-3-yl)oxy]pyridine-2-carboxylic acid

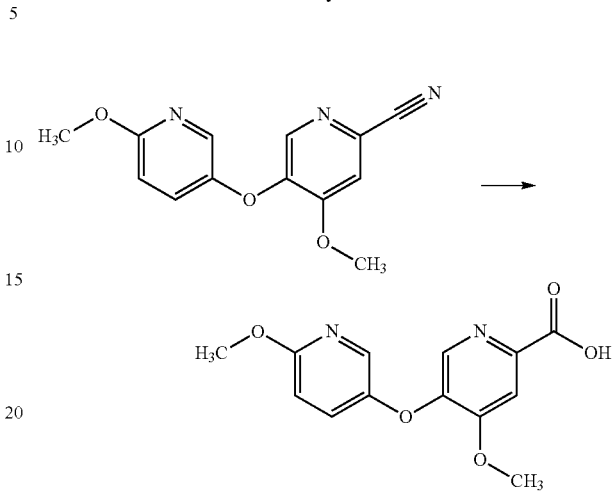

4-Methoxy-5-[(6-methoxypyridin-3-yl)oxy]pyridine-2-carbonitrile (0.85 g; 3.30 mmol) and NaOH (4 mol/L; aq. solution; 5.00 mL; 20.00 mmol) are stirred at 100° C. for 2.5 hours. After cooling to RT the reaction mixture is diluted with water and acidified to ~pH 2 using HCl (1 mol/L; aq. solution). The aqueous layer is extracted several times with EtOAc. The combined organic layers are dried over $Na_2SO_4$, filtered and concentrated under reduced pressure.

Yield: 0.56 g (61%) ESI-MS: m/z=277 [M+H]$^+$ $R_t$(HPLC): 0.69 (method 1)

Intermediate 8.1

Methyl 3-methoxy-4-{[6-(trifluoromethyl)pyridin-3-yl]oxy}benzoate

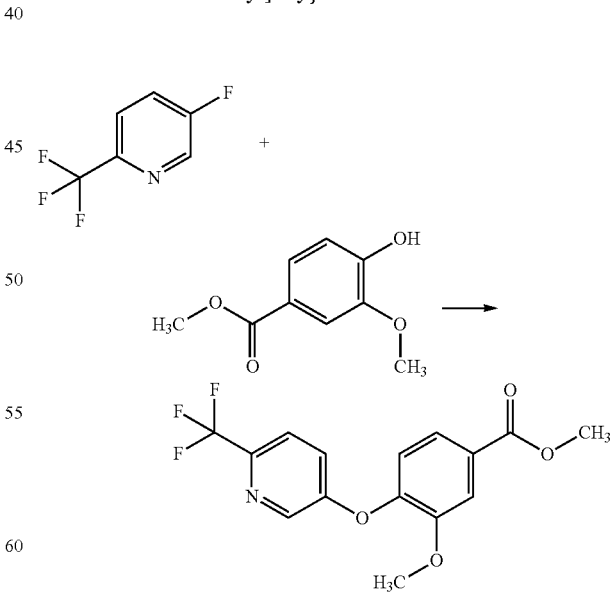

5-Fluoro-2-(trifluoromethyl)pyridine (0.15 g; 0.91 mmol), methyl 4-hydroxy-3-methoxybenzoate (0.18 g; 0.99 mmol) and potassium carbonate (0.38 g; 2.75 mmol) in DMF (5 mL) are stirred at 120° C. over night. The reaction mixture is filtered and the mother liquid is purified by RP-HPLC (ACN/water+TFA, column SunFire).

Yield: 0.21 g (71%) ESI-MS: m/z=328 [M+H]+ R$_t$(HPLC): 1.10 (method 1)

Intermediate 8.2

3-Methoxy-4-{[6-(trifluoromethyl)pyridin-3-yl]oxy}benzoic acid

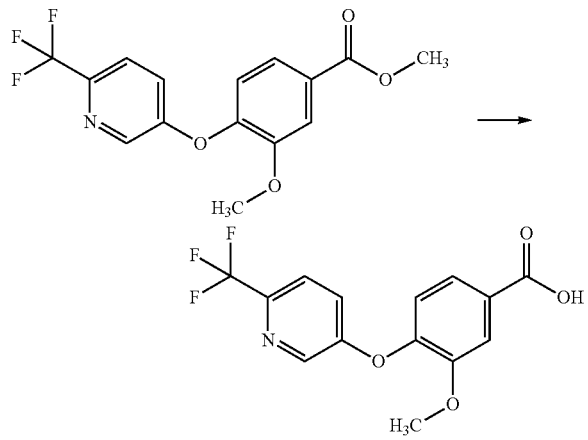

Methyl 3-methoxy-4-{[6-(trifluoromethyl)pyridin-3-yl]oxy}benzoate (0.21 g; 0.64 mmol) and NaOH (4 mol/L; aq. solution; 1.00 mL; 4.00 mmol) in MeOH (10 mL) are stirred at RT over night. HCl (4 mol/L; aq. solution; 1.00 mL; 4.00 mmol) is added and the reaction mixture is concentrated under reduced pressure. The residue is taken up in MeOH, the insoluble material is filtered off and the mother liquid is concentrated under reduced pressure.

Yield: quantitative ESI-MS: m/z=314 [M+H]+ R$_t$(HPLC): 0.99 (method 1)

Intermediate 9.1

Methyl 5-[(6-methoxypyridin-3-yl)oxy]pyridine-2-carboxylate

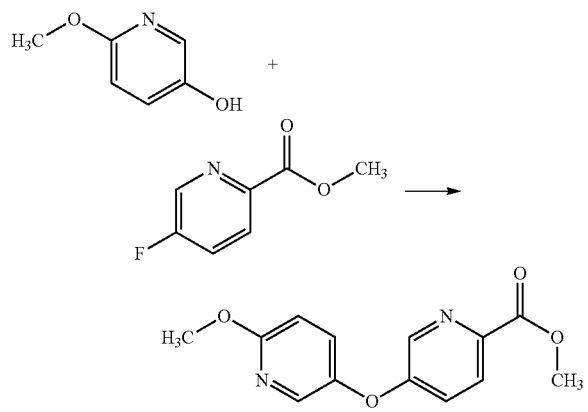

6-Methoxypyridin-3-ol (0.20 g; 1.59 mmol), methyl 5-fluoropyridine-2-carboxylate (0.25 g; 1.61 mmol) and potassium carbonate (0.67 g; 4.85 mmol) in DMF (5 mL) are stirred at 120° C. over night. The reaction mixture is filtered and the mother liquid is purified by RP-HPLC (ACN/water+TFA, column: SunFire).

Yield: 0.14 g (34%) ESI-MS: m/z=261 [M+H]+ R$_t$(HPLC): 0.88 (method 1)

Intermediate 9.2

5-[(6-Methoxypyridin-3-yl)oxy]pyridine-2-carboxylic acid

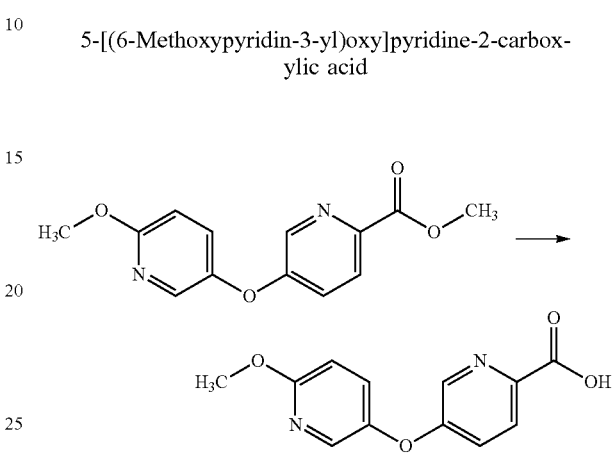

Methyl 5-[(6-methoxypyridin-3-yl)oxy]pyridine-2-carboxylate (0.14 g; 0.52 mmol) and NaOH (4 mol/L; aq. solution; 0.70 mL; 2.80 mmol) in MeOH (10 mL) are stirred at RT over night. HCl (4 mol/L; aq. solution; 0.70 mL; 2.80 mmol) is added and the reaction mixture is concentrated under reduced pressure. The residue is taken up in MeOH, the insoluble material is filtered off and the mother liquid is concentrated under reduced pressure.

Yield: 0.12 g (94%) ESI-MS: m/z=247 [M+H]+ R$_t$(HPLC): 0.76 (method 1)

Synthesis of Compounds

Example 1

6-[(2S,4S)-1-{4-[(6-Methoxypyridin-3-yl)oxy]benzoyl}-2-methylpiperidin-4-yl]-5-methylpyridazin-3-amine trifluoroacetic acid

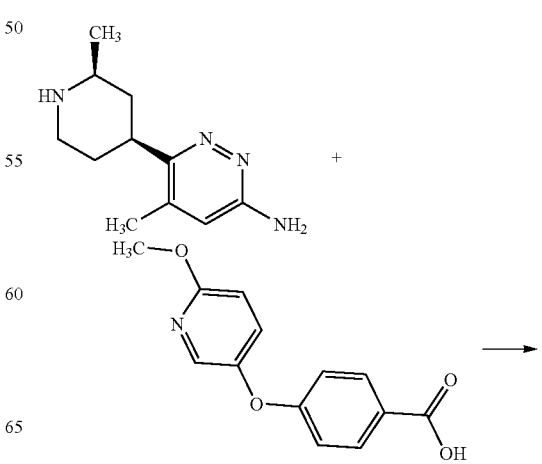

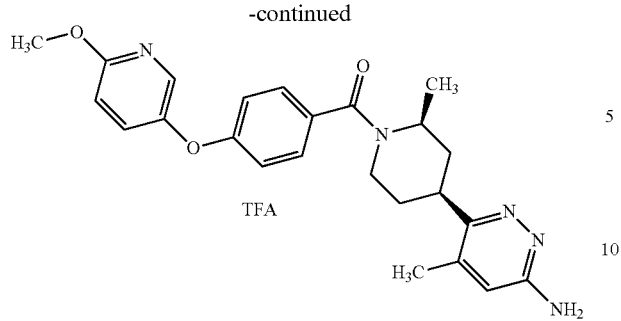

TFA

4-[(6-Methoxypyridin-3-yl)oxy]benzoic acid (23.8 mg; 0.10 mmol), 5-methyl-6-[(2S,4S)-2-methylpiperidin-4-yl]pyridazin-3-amine (20.0 mg; 0.10 mmol) and DIPEA (68.4 µL; 0.40 mmol) in DMF (2 mL) are stirred at RT, HATU (36.9 mg; 0.10 mmol) is added. After stirring over night the reaction mixture is purified by RP-HPLC (ACN/water+TFA).

Yield: 33.8 mg (64%) ESI-MS: m/z=434 [M+H]$^+$ R$_t$(HPLC): 0.58 (method 11)

Example 2

6-[(2S,4S)-1-{3-Methoxy-4-[(6-methoxypyridin-3-yl)oxy]benzoyl}-2-methylpiperidin-4-yl]-5-methylpyridazin-3-amine

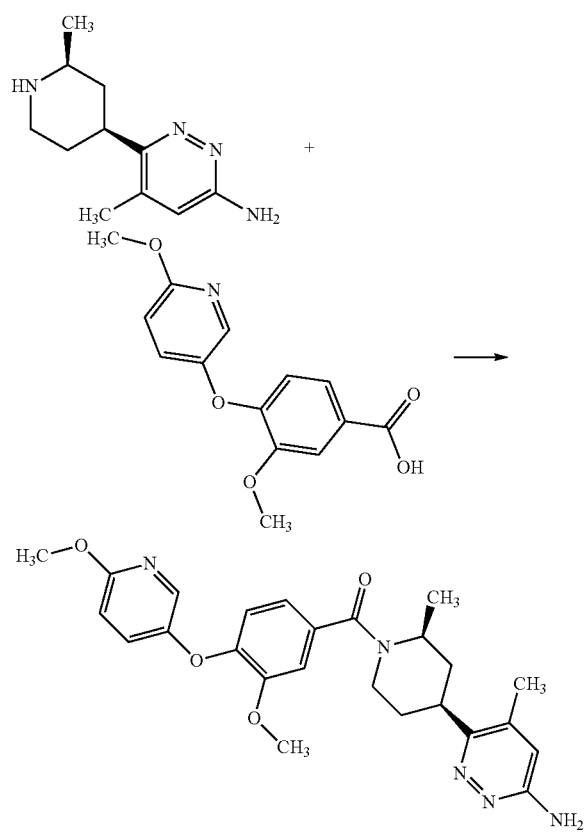

3-Methoxy-4-[(6-methoxypyridin-3-yl)oxy]benzoic acid (20.0 mg; 0.07 mmol), HATU (30.0 mg; 0.08 mmol) and DIPEA (60.0 µL; 0.35 mmol) in DMF (2 mL) are stirred at RT for 30 minutes. 5-Methyl-6-[(2S,4S)-2-methylpiperidin-4-yl]pyridazin-3-amine (15.0 mg; 0.07 mmol) is added. After stirring for 3 hours the reaction mixture is purified by RP-HPLC (ACN/water+NH$_3$).

Yield: 6.4 mg (19%) ESI-MS: m/z=464 [M+H]$^+$ R$_t$(HPLC): 0.81 (method 1)

Example 3

6-[(2S,4S)-1-{4-Methoxy-5-[(6-methoxypyridin-3-yl)oxy]pyridine-2-carbonyl}-2-methylpiperidin-4-yl]-5-methylpyridazin-3-amine

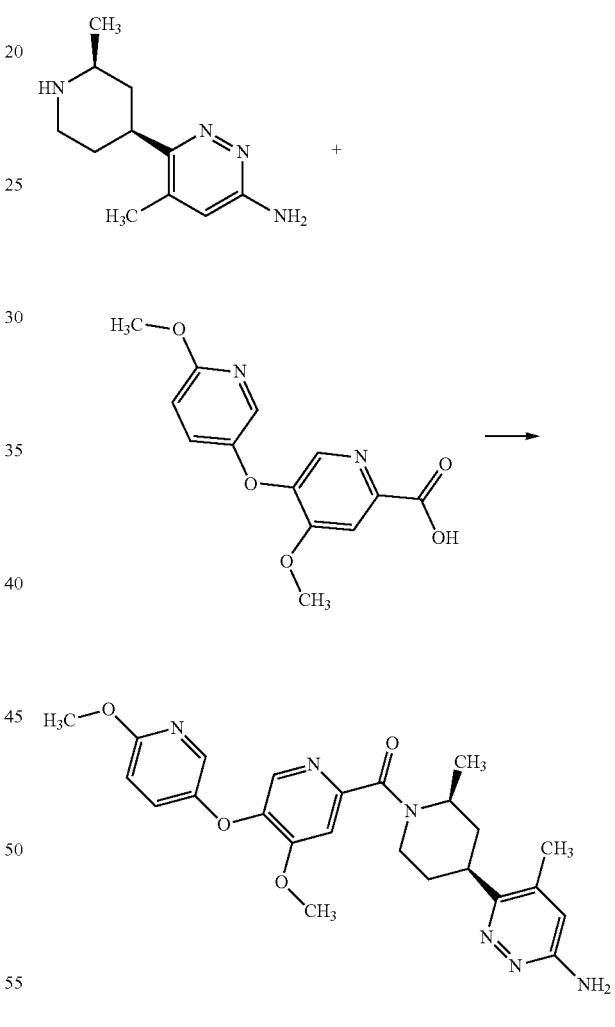

4-Methoxy-5-[(6-methoxypyridin-3-yl)oxy]pyridine-2-carboxylic acid (20.0 mg; 0.07 mmol), HATU (30.0 mg; 0.08 mmol) and DIPEA (60.0 µL; 0.35 mmol) in DMF (2 mL) are stirred at RT for 30 minutes. 5-Methyl-6-[(2S,4S)-2-methylpiperidin-4-yl]pyridazin-3-amine (15.0 mg; 0.07 mmol) is added. After stirring over night at RT the reaction mixture is purified by RP-HPLC (ACN/water+NH$_3$).

Yield: 2.0 mg (6%) ESI-MS: m/z=465 [M+H]$^+$ R$_t$(HPLC): 0.76 (method 1)

Example 4

6-[(2S,4S)-1-(3-Methoxy-4-{[6-(trifluoromethyl)pyridin-3-yl]oxy}benzoyl)-2-methylpiperidin-4-yl]-5-methylpyridazin-3-amine

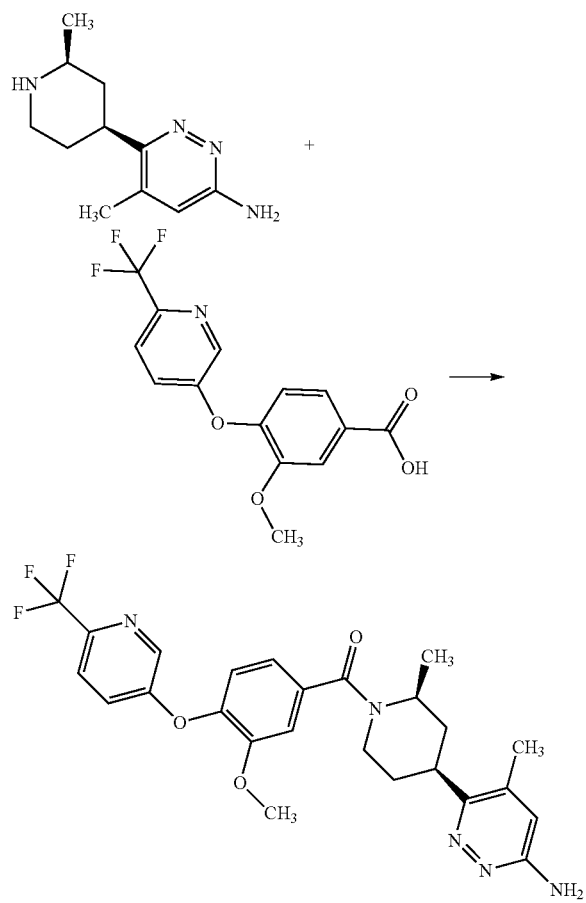

3-Methoxy-4-{[6-(trifluoromethyl)pyridin-3-yl]oxy}benzoic acid (20.0 mg; 0.06 mmol), HATU (25.0 mg; 0.07 mmol) and DIPEA (60.0 µL; 0.35 mmol) in DMF (2 mL) are stirred at RT for 30 minutes. 5-Methyl-6-[(2S,4S)-2-methylpiperidin-4-yl]pyridazin-3-amine (15.0 mg; 0.07 mmol) is added. After stirring for 2 hours at RT the reaction mixture is purified by RP-HPLC (ACN/water+NH₃).

Yield: 16.2 mg (51%) ESI-MS: m/z=502 [M+H]⁺ R$_f$(HPLC): 0.86 (method 1)

Example 5

6-(1-{4-Methoxy-5-[(6-methoxypyridin-3-yl)oxy]pyridine-2-carbonyl}piperidin-4-yl)pyridazin-3-amine trifluoracetic acid

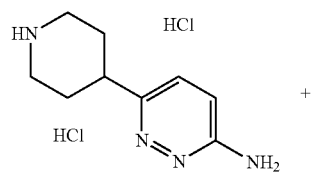

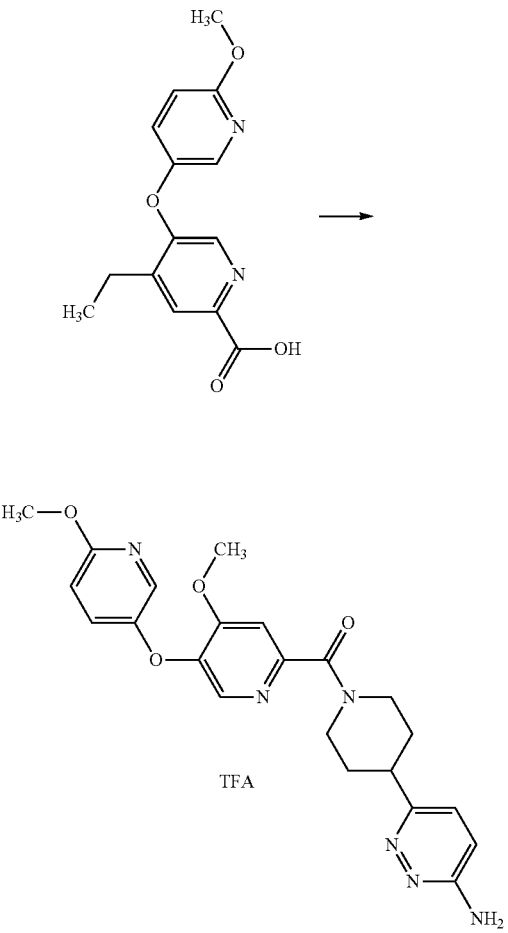

4-Methoxy-5-[(6-methoxypyridin-3-yl)oxy]pyridine-2-carboxylic acid (60.0 mg; 0.22 mmol), HATU (85.0 mg; 0.22 mmol) and DIPEA (150.0 µL; 0.88 mmol) in DMF (3 mL) are stirred at RT for 30 minutes. 6-(Piperidin-4-yl)pyridazin-3-amine dihydrochloride (60.0 mg; 0.24 mmol) is added. After stirring over night at RT the reaction mixture is purified by RP-HPLC (ACN/water+TFA).

Yield: 71.4 mg (60%) ESI-MS: m/z=437 [M+H]⁺ R$_f$(HPLC): 0.72 (method 1)

Example 6

6-[(3R,4R)-1-{3-Methoxy-4-[(6-methoxypyridin-3-yl)oxy]benzoyl}-3-methylpiperidin-4-yl]-5-methylpyridazin-3-amine

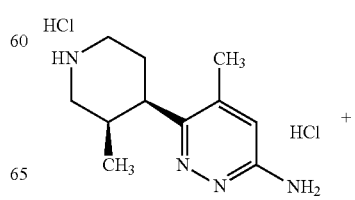

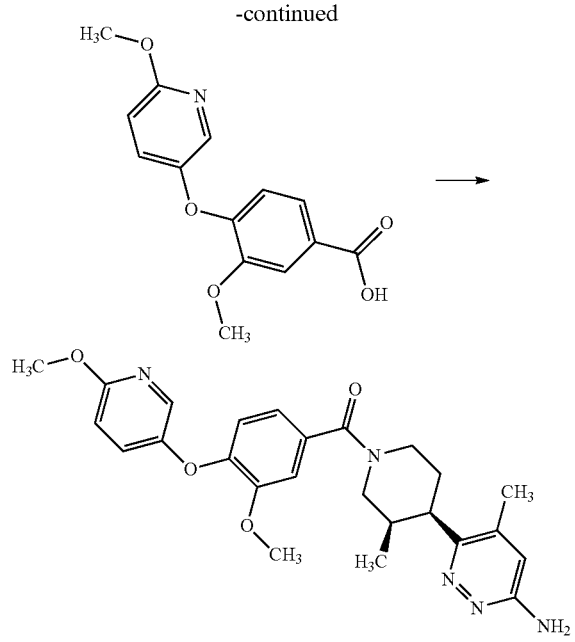

3-Methoxy-4-[(6-methoxypyridin-3-yl)oxy]benzoic acid (20.0 mg; 0.07 mmol), HATU (30.0 mg; 0.08 mmol) and DIPEA (60.0 μL; 0.35 mmol) in DMF (2 mL) are stirred at RT for 30 minutes. 5-Methyl-6-[(3R,4R)-3-methylpiperidin-4-yl]pyridazin-3-amine dihydrochloride (22.0 mg; 0.08 mmol) is added. After stirring over night at RT the reaction mixture is purified by RP-HPLC (ACN/water+NH$_3$).

Yield: 20.3 mg (60%) ESI-MS: m/z=464 [M+H]$^+$ R$_t$(HPLC): 0.79 (method 1)

Example 7

6-(1-{4-[(6-Methoxypyridin-3-yl)oxy]benzoyl}piperidin-4-yl)-5-methylpyridazin-3-amine trifluoroacetic acid

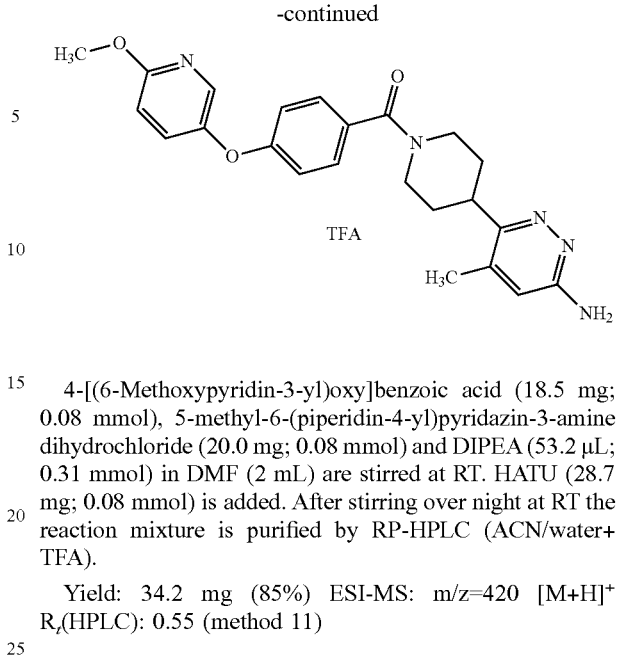

4-[(6-Methoxypyridin-3-yl)oxy]benzoic acid (18.5 mg; 0.08 mmol), 5-methyl-6-(piperidin-4-yl)pyridazin-3-amine dihydrochloride (20.0 mg; 0.08 mmol) and DIPEA (53.2 μL; 0.31 mmol) in DMF (2 mL) are stirred at RT. HATU (28.7 mg; 0.08 mmol) is added. After stirring over night at RT the reaction mixture is purified by RP-HPLC (ACN/water+TFA).

Yield: 34.2 mg (85%) ESI-MS: m/z=420 [M+H]$^+$ R$_t$(HPLC): 0.55 (method 11)

Example 8

6-(1-{3-Methoxy-4-[(6-methoxypyridin-3-yl)oxy]benzoyl}piperidin-4-yl)-5-methylpyridazin-3-amine trifluoroacetic acid

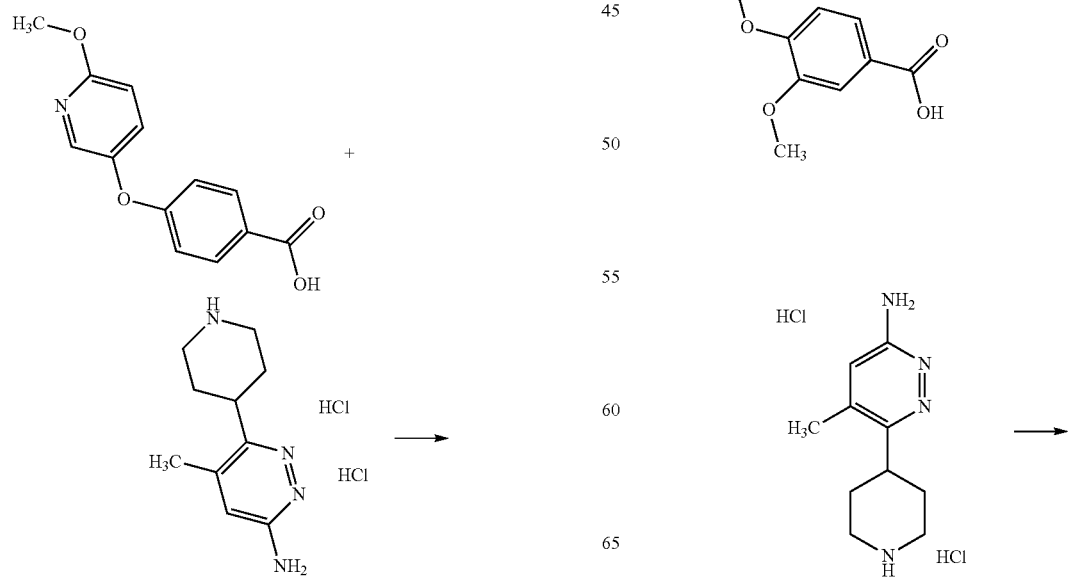

-continued

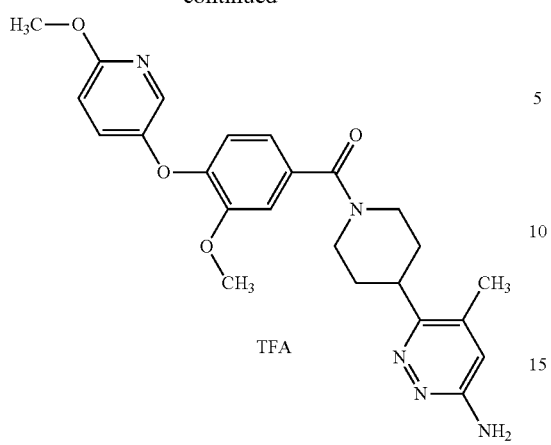

TFA

3-Methoxy-4-[(6-methoxypyridin-3-yl)oxy]benzoic acid (20.0 mg; 0.07 mmol), HATU (30.0 mg; 0.08 mmol) and DIPEA (60.0 µL; 0.35 mmol) in DMF (2 mL) are stirred at RT for 30 minutes. 5-Methyl-6-(piperidin-4-yl)pyridazin-3-amine dihydrochloride (20.0 mg; 0.08 mmol) is added. After stirring for 3 hours at RT the reaction mixture is purified by RP-HPLC (ACN/water+TFA).

Yield: 11.8 mg (29%) ESI-MS: m/z=450 [M+H]$^+$ R$_f$(HPLC): 0.79 (method 1)

Example 9

6-(1-{4-Methoxy-5-[(6-methoxypyridin-3-yl)oxy]pyridine-2-carbonyl}piperidin-4-yl)-5-methylpyridazin-3-amine trifluoracetic acid

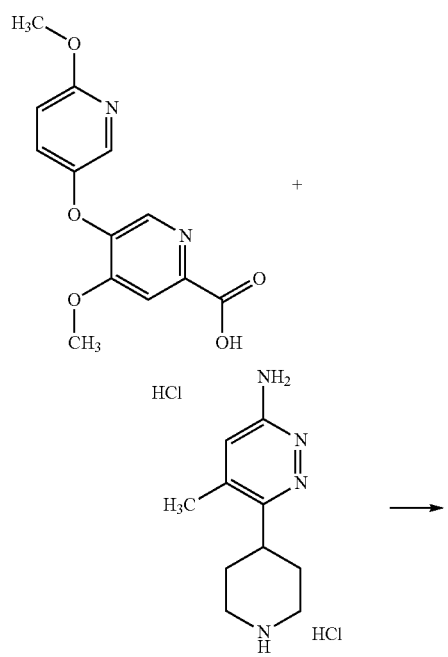

-continued

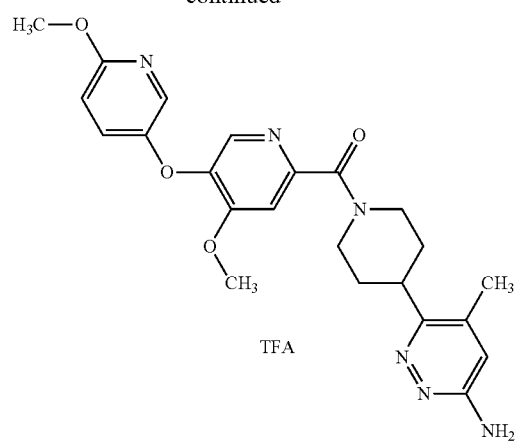

TFA

4-Methoxy-5-[(6-methoxypyridin-3-yl)oxy]pyridine-2-carboxylic acid (20.0 mg; 0.07 mmol), HATU (30.0 mg; 0.08 mmol) and DIPEA (60.0 µL; 0.35 mmol) in DMF (2 mL) are stirred at RT for 30 minutes. 5-Methyl-6-(piperidin-4-yl)pyridazin-3-amine dihydrochloride (20.0 mg; 0.08 mmol) is added. After stirring over night at RT the reaction mixture is purified by RP-HPLC (ACN/water+TFA).

Yield: 14.5 mg (36%) ESI-MS: m/z=451 [M+H]$^+$ R$_f$(HPLC): 0.74 (method 1)

Example 10

6-[(3R,4R)-1-{5-[(6-Methoxypyridin-3-yl)oxy]pyridine-2-carbonyl}-3-methylpiperidin-4-yl]-5-methylpyridazin-3-amine

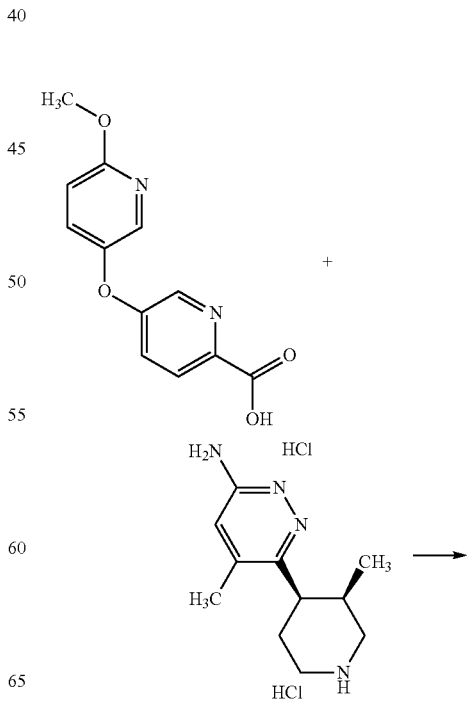

-continued

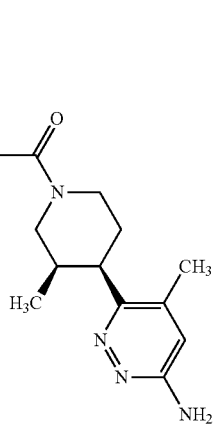

5-[(6-Methoxypyridin-3-yl)oxy]pyridine-2-carboxylic acid (20.0 mg; 0.08 mmol), HATU (31.0 mg; 0.08 mmol) and DIPEA (60.0 µL; 0.35 mmol) in DMF (2 mL) are stirred at RT for 30 minutes. 5-Methyl-6-[(3R,4R)-3-methylpiperidin-4-yl]pyridazin-3-amine dihydrochloride (25.0 mg; 0.09 mmol) is added. After stirring for 3 days at RT the reaction mixture is purified by RP-HPLC (ACN/water+NH$_3$).

Yield: 7.9 mg (22%) ESI-MS: m/z=435 [M+H]$^+$ R$_t$(HPLC): 0.75 (method 1)

Assessment of Biological Activity

Biological Assays
The biological activity of compounds is determined by the following methods:
Assay A: Determination of TRPC6 Inhibition
HEK293 cells transfected with a plasmid expressing human TRPC6 are used for a patch clamp assay. Patch clamp experiments permit the detection of currents through TRPC6 channels in cellular systems as mentioned above. For whole-cell patch clamp recordings, a glass capillary electrode filled with electrolyte is brought into contact with a single cell and a high-resistance (gigaohm) seal is established with the cell membrane. The membrane is then ruptured to achieve the whole-cell configuration, permitting control of the intracellular electrical potential and measurement of electrical currents across the cell membrane using an amplifier connected to the electrode. A perfusion system permits control of the extracellular solution, including the addition of inhibitors and activators of TRPC6 channels. The TRPC6 current can be activated by 10 µM ethyl 8-fluoro-1H,2H,3H,4H,5H-pyrido[4,3-b]indole-2-carboxylate (commercially available, MFCD02930345) in the extracellular solution.

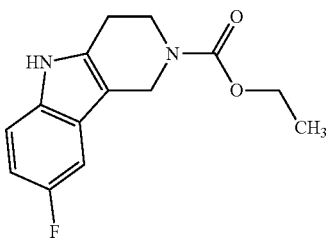 [SMILES: CCOC(=O)N1CCc2[nH]c3ccc(F)cc3c2C1]

For the characterization of TRPC6 inhibitors, TRPC6 expression was induced for 20-48 hours, cells were removed from growth plates, and replated at low density (to attain good single-cell physical separation) in small dishes for measurement. Patch clamp recordings were performed in the whole-cell configuration at a holding potential of −40 mV. Every 1.5 seconds, a 400 ms voltage ramp was applied from −80 to +80 mV, flanked by 50 ms constant segments at −80 and +80 mV, respectively. TRPC6-mediated currents were quantified during those constant segments at −80 mV and +80 mV. The internal (pipette) solution consisted of 140 mM cesium aspartate, 10 mM EGTA, 1.91 mM CaCl$_2$, 2.27 mM MgCl$_2$ and 10 mM HEPES, pH 7.2 with CsOH, 40 nM calculated free Ca$^{2+}$. The external (bath) solution consisted of 145 mM NaCl, 4.5 mM KCl, 3 mM MgCl$_2$, 10 mM HEPES, 10 mM glucose, 1 mM EGTA, pH 7.4 with NaOH. TRPC6 expressing cells were pre-incubated with potential inhibitors at either 30 nM or at various concentrations (for concentration-response-curves) or vehicle for at least 3 h and both maximal inward and outward currents were determined after addition of ethyl 8-fluoro-1H,2H,3H,4H,5H-pyrido[4,3-b]indole-2-carboxylate. Percent current inhibition was calculated from the average inward current densities of treated and vehicle cells. Current densities were calculated as absolute current normalized with respect to the individual cell's membrane capacitance as a surrogate parameter for cellular surface area. The number of cells measured for each group was chosen in a way that an average of 50% current inhibition with respect to the vehicle group would yield a statistically significant difference ($p<0.05$) in 90% of the cases based on the variability in current expression between cells. For the estimation of half-inhibitory concentrations, the Hill equation was fitted to the average % percent inhibition values at a series of concentrations of a specific compound.

TABLE 3

Antagonist effects of compounds of the invention against human TRPC6 (%-inhibition at 30 nM) using a patch clamp assay.

| Compound No. | % inhibition @ 30 nM |
| --- | --- |
| 1 | 81 |
| 2 | 60 |
| 4 | 12 |
| 5 | 27 |
| 6 | 72 |
| 7 | 61 |
| 8 | 37 |
| 9 | 51 |

The compounds of the invention show favourable metabolic stability in human microsomes.
Methods of Therapeutic Use
The inhibition of TRPC6 is an attractive means for preventing and treating a variety of diseases or conditions that are exacerbated by TRPC6 activity. The compounds disclosed herein effectively inhibit TRPC6 activity. In particular, the compounds of the invention are selective ion channel inhibitors and have good metabolic stability in human microsomes. More particularly, the compounds of the invention have very good potency and selectivity on the TRPC6 channel as compared to other TRP channels including TRPC3, TRPC5 and TRPC7. Thus, the compounds of the invention are useful for the treatment of diseases and conditions as described in the Background and Detailed Description section, including the following conditions and diseases:
cardiac conditions (e.g., cardiac hypertrophy), hypertension (e.g., primary or secondary), pulmonary arterial hypertension (e.g., IPAH), a neurodegenerative disease or disorder (e.g., Alzheimer's disease (AD), Parkinson's disease, Huntington's disease, amyotrophic lateral sclerosis (ALS), and other brain disorders caused by trauma or other insults including aging), inflammatory diseases (e.g., asthma, emphysema, chronic obstructive pulmonary disease, rheumatoid arthritis, osteoarthritis, inflammatory bowel disease, multiple sclerosis, muscular dystrophy, Duchenne's muscular dystrophy, and disorders of the immune system), preeclampsia and pregnancy-induced hypertension, kidney diseases (focal segmental glomerulosclerosis, nephrotic syndrome, diabetic nephropathy or diabetic kidney disease, chronic kidney disease (CKD), renal insufficiency, end stage renal disease, nonalcoholic steatohepatitis (NASH), minimal change disease, ischemia or an ischemic reperfusion injury, cancer, metabolic disorders such as diabetes, idiopathic pulmonary fibrosis (IPF), acute respiratory disease syndrome (ARDS)/severe acute respiratory syndrome (SARS), sepsis, severe sepsis and septic shock Methods for preventing or treating any of the foregoing or following diseases and conditions include treating any of the symptoms associated with these diseases or conditions. For example, methods for treating kidney disease contemplate treating symptoms including, but not limited to, secondary hypertension, proteinuria, lipiduria, hypercholesterolemia, hyperlipidemia, and coagulation abnormalities.

Because of the important role that calcium regulation plays in many cellular processes including cellular activation, cytoskeletal rearrangement, gene expression, cellular trafficking and apoptotic cell death, calcium dyshomeostasis is implicated in the many diseases and disorders. These diseases and disorders include neurological and neurodegenerative diseases and disorders; inflammatory diseases and disorders such as inflammatory bowel disease and Crohn's disease; kidney disease such as hypercalcemia, kidney stones, and polycystic kidney disease; metabolic diseases and disorders including obesity and diabetes; liver and kidney diseases and disorders; cardiovascular diseases and disorders including hypertension; respiratory diseases including COPD, IPAH, and asthma, and cancers, including cancers of the brain, breast, kidney, cervix, prostate, gastrointestinal tract, skin, and epithelia.

These disorders have been well characterized in man, but also exist with a similar etiology in other mammals, and can be treated by pharmaceutical compositions of the present invention.

Accordingly, a compound of the invention, as described herein, or a pharmaceutically acceptable salt thereof may be used for the preparation of a medicament for treating a disease or disorder mediated by TRPC6, including those mentioned above and in the Background and Detailed Description sections.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of the invention (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regimen.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The compounds of the invention may be used alone or in combination of one or more additional therapeutic agents. Nonlimiting examples of additional therapeutic agents may include:

angiotensin II receptor antagonists (angiotensin receptor blockers (ARBs)) such as candesartan, eprosartan, candesartan, irbesartan, losartan, olmesartan, telmisartan, valsartan, azilsartan, and medoxomil;

angiotensin converting enzyme inhibitors (e.g., benazepril, captopril, enalapril, fosinopril, lisinopril, moexipril, and perindopril);

antidiabetics such as alpha-glucosidase inhibitors (e.g., miglitol and acarbose), amylin analogs (e.g., pramlintide), dipeptidyl peptidase 4 inhibitors (e.g., alogliptin, sitagliptin, saxagliptin, and linagliptin), incretin mimetics (e.g., liraglutide, exenatide, liraglutide, exenatide, dulaglutide, albiglutide, and lixisenatide), insulin, meglitinides (e.g., repaglinide and nateglinide), biguanides (e.g., metformin); SGLT-2 inhibitors (e.g., canagliflozin, empagliflozin, and dapagliflozin), sulfonylureas (e.g., chlorpropamide, glimepiride, glyburide, glipizide, glyburide, tolazamide, and tolbutamide), and thiazolidinediones (e.g., rosiglitazone and pioglitazone);

bronchodilators including short-acting and long-action beta agonists (e.g., albuterol, levalbuterol, salmeterol, formoterol, and arformoterol) and short- and long-acting anticholinergics (ipratropium, tiotropium, umeclidinium, glycopyrrolatei), and aclidinium).

steroids such as fluticasone and budesonide;

When used as combination treatment of a pharmaceutical combination, the compounds of the invention and the one or more additional agents can be administered in the same dosage form or different dosage forms. The compounds of the invention and the one or more additional agents can be administered simultaneously or separately, as part of a regimen.

What is claimed is:

1. A compound of formula (I)

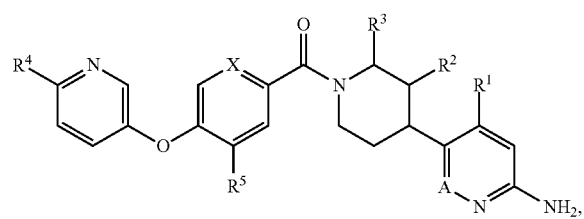

(I)

wherein

A is selected from CH or N;

X is selected from CH or N;

$R^1$ is selected from the group consisting of H, —CH$_3$ and —OCH$_3$;

$R^2$ is selected from the group consisting of H and —CH$_3$;

$R^3$ is selected from the group consisting of H and —CH$_3$; or $R^2$ and $R^3$ together denote a —(CH$_2$)$_n$— bridge, wherein n denotes the number 2, 3, 4 or 5, and wherein optionally one —CH$_2$— member is replaced by O, S, —NH— or —N(CH)$_3$—, or the —CH($R^3$)-($R^2$)CH— substructure in formula (I) is replaced by a 5-membered heteroaryl group selected from the group consisting of furan, thiophen, pyrrol and N-methyl-pyrrol, which are condensed with the piperine ring of formula (I);

$R^4$ is selected from the group consisting of H, —CF$_3$, and —OCH$_3$;

$R^5$ is selected from the group consisting of H, —F and —OCH$_3$;

and salts thereof.

2. The compound according to claim 1, wherein

A is selected from CH or N;

X is selected from CH or N;

$R^1$ is selected from the group consisting of H, —CH$_3$ and —OCH$_3$, $R^2$ denotes H and $R^3$ is selected from the group consisting of H and —CH$_3$; or $R^2$ denotes -CH$_3$ and $R^3$ denotes H;

$R^4$ is selected from the group consisting of H, —CF$_3$, and —OCH$_3$;

$R^5$ is selected from the group consisting of H, —F and —OCH$_3$;

and the salts thereof.

3. The compound according to claim 1, wherein

A denotes N;

$R^1$ is selected from the group consisting of H and —CH$_3$ $R^4$ is selected from the group consisting of —CF$_3$ and —OCH$_3$;

and the salts thereof.

4. The compound according to claim 1, wherein

A denotes N;

$R^1$ is selected from the group consisting of H and —CH$_3$ $R^4$ denotes —OCH$_3$;

and the salts thereof.

5. The compound according to claim 1, wherein

A denotes N;

$R^1$ is selected from the group consisting of H and —CH$_3$

X denotes CH;

$R^4$ denotes —OCH$_3$;

$R^5$ denotes H;

and the salts thereof.

6. The compound according to claim 1, wherein

A denotes N;

$R^1$ is selected from the group consisting of H and —CH$_3$

X denotes N;

$R^4$ denotes —OCH$_3$;

$R^5$ denotes H;

and the salts thereof.

7. The compound of formula (Ia), (Ib) or (Ic) according to claim 1,

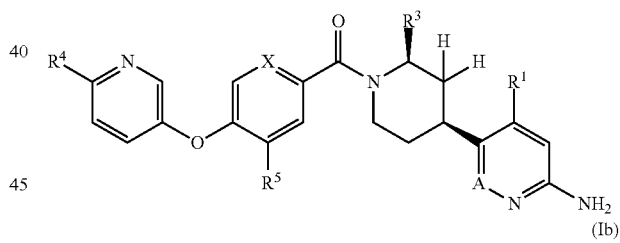

(Ia)

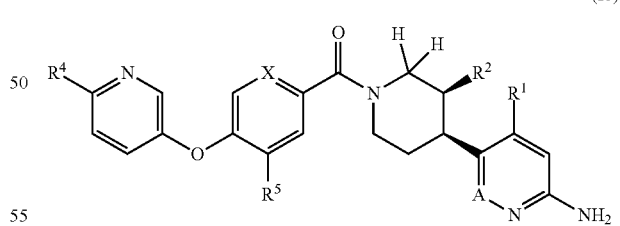

(Ib)

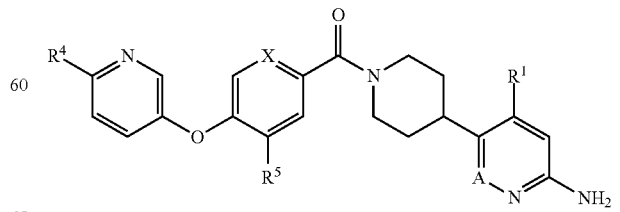

(Ic)

and the salts thereof.

8. The compound according to claim 1, selected from the group consisting of:

| Cpd No. | Structure | Compound Name |
|---|---|---|
| 1 | 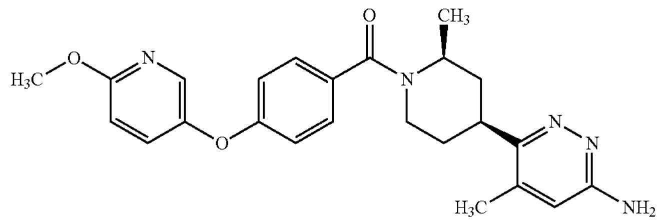 [SMILES: COc1ccc(Oc2ccc(C(=O)N3CC[C@H](c4nnc(N)cc4C)C[C@@H]3C)cc2)cn1] | 6-[(2S,4S)-1-{4-[(6-Methoxypyridin-3-yl)oxy]benzoyl}-2-methylpiperidin-4-yl]-5-methylpyridazin-3-amine |
| 2 | 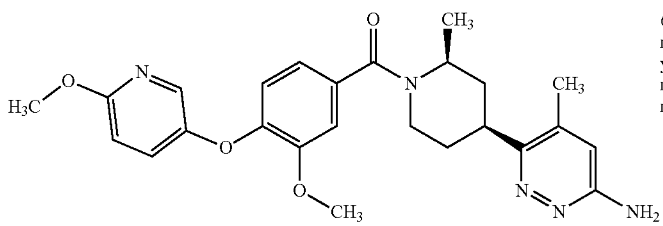 [SMILES: COc1ccc(Oc2ccc(C(=O)N3CC[C@H](c4nnc(N)cc4C)C[C@@H]3C)cc2OC)cn1] | 6-[(2S,4S)-1-{3-Methoxy-4-[(6-methoxypyridin-3-yl)oxy]benzoyl}-2-methylpiperidin-4-yl]-5-methylpyridazin-3-amine |
| 3 | 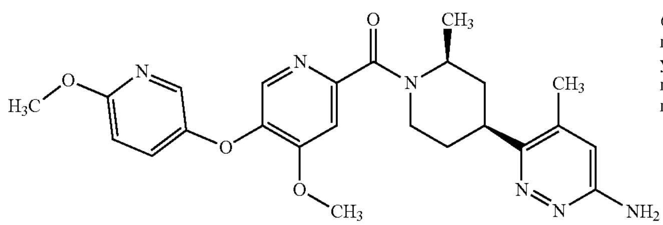 [SMILES: COc1ccc(Oc2cnc(C(=O)N3CC[C@H](c4nnc(N)cc4C)C[C@@H]3C)cc2OC)cn1] | 6-[(2S,4S)-1-{4-Methoxy-5-[(6-methoxypyridin-3-yl)oxy]pyridine-2-carbonyl}-2-methylpiperidin-4-yl]-5-methylpyridazin-3-amine |
| 4 | 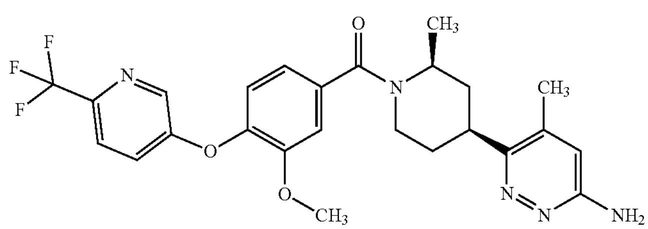 [SMILES: COc1cc(C(=O)N2CC[C@H](c3nnc(N)cc3C)C[C@@H]2C)ccc1Oc1ccc(C(F)(F)F)nc1] | 6-[(2S,4S)-1-(3-Methoxy-4-{[6-(trifluoromethyl)pyridin-3-yl]oxy}benzoyl)-2-methylpiperidin-4-yl]-5-methylpyridazin-3-amine |
| 5 | 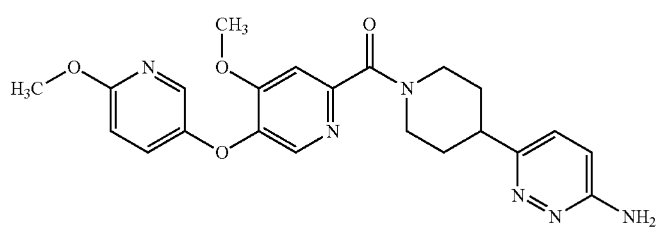 [SMILES: COc1ccc(Oc2cnc(C(=O)N3CCC(c4ccc(N)nn4)CC3)cc2OC)cn1] | 6-(1-{4-Methoxy-5-[(6-methoxypyridin-3-yl)oxy]pyridine-2-carbonyl}piperidin-4-yl)pyridazin-3-amine |
| 6 | 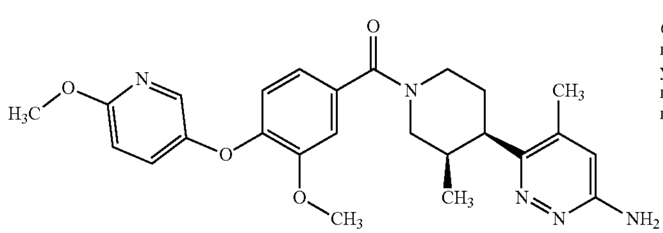 [SMILES: COc1ccc(Oc2ccc(C(=O)N3CC[C@@H](c4nnc(N)cc4C)[C@@H](C)C3)cc2OC)cn1] | 6-[(3R,4R)-1-{3-Methoxy-4-[(6-methoxypyridin-3-yl)oxy]benzoyl}-3-methylpiperidin-4-yl]-5-methylpyridazin-3-amine |

| Cpd No. | Structure | Compound Name |
|---|---|---|
| 7 | 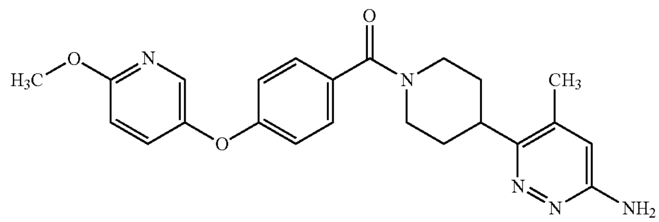 [SMILES: COc1ccc(Oc2ccc(C(=O)N3CCC(c4nnc(N)cc4C)CC3)cc2)cn1] | 6-(1-{4-[(6-Methoxypyridin-3-yl)oxy]benzoyl}piperidin-4-yl)-5-methylpyridazin-3-amine |
| 8 | 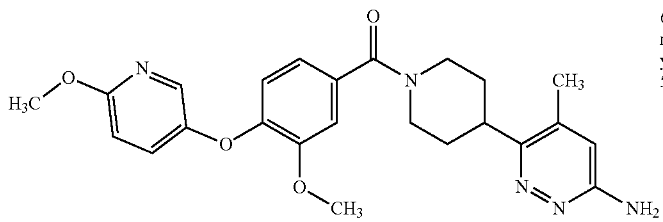 [SMILES: COc1ccc(Oc2ccc(C(=O)N3CCC(c4nnc(N)cc4C)CC3)cc2OC)cn1] | 6-(1-{3-Methoxy-4-[(6-methoxypyridin-3-yl)oxy]benzoyl}piperidin-4-yl)-5-methylpyridazin-3-amine |
| 9 | 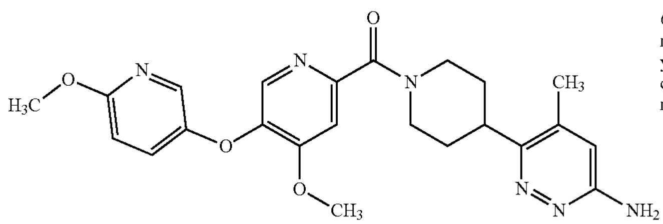 [SMILES: COc1ccc(Oc2cnc(C(=O)N3CCC(c4nnc(N)cc4C)CC3)cc2OC)cn1] | 6-(1-{4-Methoxy-5-[(6-methoxypyridin-3-yl)oxy]pyridine-2-carbonyl}piperidin-4-yl)-5-methylpyridazin-3-amine, and |
| 10 | 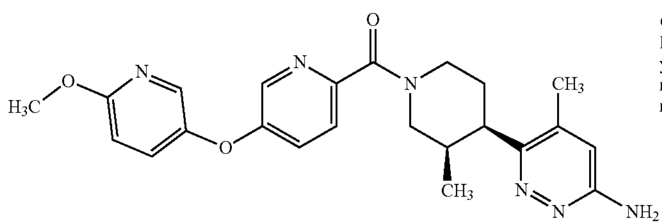 [SMILES: COc1ccc(Oc2ccc(C(=O)N3CC[C@@H](c4nnc(N)cc4C)[C@@H](C)C3)nc2)cn1] | 6-[(3R,4R)-1-{5-[(6-Methoxypyridin-3-yl)oxy]pyridine-2-carbonyl}-3-methylpiperidin-4-yl]-5-methylpyridazin-3-amine. |

9. A pharmaceutically acceptable salt of a compound according to claim 8.

10. A pharmaceutical composition comprising a compound of claim 1, or a pharmaceutically acceptable salt thereof, and optionally a pharmaceutically acceptable excipient.

11. The pharmaceutical composition according to claim 10, further comprising one or more additional therapeutic agents.

12. A method for treating a disease or disorder that can be alleviated by TRPC6 inhibition comprising administering a therapeutically effective amount of a compound according to claim 1, or a pharmaceutically acceptable salt thereof, to patient in need thereof.

13. A method for treating a disease or disorder that can be alleviated by TRPC6 modulation, the method comprising administering a pharmaceutically effective amount of a compound according to claim 1, or a pharmaceutically acceptable salt thereof, to a patient in need thereof.

* * * * *